(12) United States Patent
Mooney et al.

(10) Patent No.: US 6,827,710 B1
(45) Date of Patent: Dec. 7, 2004

(54) MULTIPLE LUMEN ACCESS DEVICE

(75) Inventors: Charles R. Mooney, Costa Mesa, CA (US); Robert Pecor, Aliso Viejo, CA (US); Donald E. Bobo, Jr., Santa Ana, CA (US); Michael J. Higgins, Trabuco Canyon, CA (US); Manouchehr A. Miraki, Laguna Hills, CA (US); Erik E. Bulman, Mission Viejo, CA (US); Gary R. Willoughby, Castle Rock, CO (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/329,002

(22) Filed: Jun. 8, 1999

Related U.S. Application Data

(63) Continuation-in-part of application No. 08/953,105, filed on Oct. 17, 1997, now abandoned, which is a continuation-in-part of application No. 08/756,763, filed on Nov. 26, 1996, now abandoned.

(51) Int. Cl.$^7$ .............................................. A61M 31/00
(52) U.S. Cl. ................... 604/500; 604/43; 604/167.06; 604/523
(58) Field of Search ................................ 604/500, 506, 604/507–508, 158, 164.01–164.07, 164.13, 165.01, 165.02, 167.01–167.05, 167.06, 171, 246–277, 264, 523, 43; 251/905

(56) References Cited

U.S. PATENT DOCUMENTS

| | | | |
|---|---|---|---|
| 1,696,018 A | * | 12/1928 | Schellberg ................... 604/39 |
| 4,233,984 A | * | 11/1980 | Walling ................. 128/207.14 |
| 4,299,217 A | | 11/1981 | Sagae et al. |
| 4,343,844 A | | 8/1982 | Thayer et al. |
| 4,406,656 A | | 9/1983 | Hattler et al. |
| 4,451,252 A | * | 5/1984 | Martin ........................ 604/43 |
| 4,601,701 A | | 7/1986 | Mueller, Jr. |
| 4,670,009 A | | 6/1987 | Bullock |
| 4,705,501 A | | 11/1987 | Wigness et al. |
| 4,758,221 A | | 7/1988 | Jureidini |
| 4,776,841 A | | 10/1988 | Catalano |
| 4,795,439 A | | 1/1989 | Guest |
| 4,842,582 A | | 6/1989 | Mahurkar |

(List continued on next page.)

FOREIGN PATENT DOCUMENTS

| | | |
|---|---|---|
| DE | 30 35 243 A1 | 3/1982 |
| DE | 38 33 359 A1 | 4/1990 |
| EP | 0 000 041 | 4/1981 |

(List continued on next page.)

*Primary Examiner*—LoAn H. Thanh
(74) *Attorney, Agent, or Firm*—Edwards Lifesciences

(57) ABSTRACT

A multiple lumen access device for use in providing a single entry port into the human body for selectively introducing medical implements therethrough and for providing simultaneous auxiliary access into the body. The multiple lumen access device includes a multi-lumen sheath which may have an outer tube and structure defining a device lumen located therein. The inner structure may be an inner wall or inner tube. The outer tube and inner structure are located so as to define at least one auxiliary lumen. Some embodiments include flexible inner walls which can be flexed between relaxed and expanded/contracted positions wherein the relative cross-sectional areas of the device lumen and auxiliary lumens are varied. The access device further includes a valve which provides sealing of the device lumen. The valve may be provided in a lumen junction housing or separate from the housing either permanently or removably connected with the device lumen. Alternatively, a multi-lumen sheath may be passed through a valve leading to a conventional introducer. The valve may also be molded separately as a rigid insert and retained in a cavity formed in a flexible junction housing. In other embodiments, the multiple lumen access device is formed by introduction of the elongated implement coaxially within a tubular single lumen sheath.

57 Claims, 31 Drawing Sheets

U.S. PATENT DOCUMENTS

| | | |
|---|---|---|
| 4,846,791 A | 7/1989 | Hattler et al. |
| 4,894,057 A | 1/1990 | Howes |
| 4,906,232 A | 3/1990 | Reynolds |
| 4,906,496 A | 3/1990 | Hosono et al. |
| 4,968,307 A | 11/1990 | Dake et al. |
| 5,021,044 A | 6/1991 | Sharkawy |
| 5,025,778 A | 6/1991 | Silverstein et al. |
| 5,053,004 A | 10/1991 | Markel et al. |
| 5,092,846 A * | 3/1992 | Nishijima et al. |
| 5,106,368 A | 4/1992 | Uldall et al. |
| 5,149,330 A | 9/1992 | Brightbill |
| 5,156,596 A | 10/1992 | Balbierz et al. |
| 5,158,540 A | 10/1992 | Wijay et al. |
| 5,163,906 A | 11/1992 | Ahmadi |
| 5,207,648 A | 5/1993 | Gross |
| 5,215,527 A | 6/1993 | Beck et al. |
| 5,219,335 A | 6/1993 | Willard et al. |
| 5,246,016 A | 9/1993 | Lieber et al. |
| 5,250,038 A | 10/1993 | Melker et al. |
| 5,295,962 A | 3/1994 | Crocker et al. |
| 5,318,532 A * | 6/1994 | Frassica .................. 604/97.01 |
| 5,328,480 A | 7/1994 | Melker et al. |
| 5,360,414 A | 11/1994 | Yarger |
| 5,364,376 A | 11/1994 | Horzewski et al. |
| 5,364,377 A | 11/1994 | O'Neil |
| 5,378,230 A | 1/1995 | Mahurkar |
| 5,391,152 A | 2/1995 | Patterson |
| 5,403,291 A | 4/1995 | Abrahamson |
| 5,435,308 A | 7/1995 | Gallup et al. |
| 5,451,206 A * | 9/1995 | Young |
| 5,456,673 A | 10/1995 | Ziegler et al. |
| 5,464,398 A | 11/1995 | Haindl |
| 5,472,417 A | 12/1995 | Martin et al. |
| 5,472,418 A * | 12/1995 | Palestrant |
| 5,527,292 A | 6/1996 | Adams et al. |
| 5,599,324 A | 2/1997 | McAlister et al. |
| 5,601,603 A | 2/1997 | Illi |
| 5,607,462 A | 3/1997 | Imran |
| 5,700,251 A | 12/1997 | Miyauchi et al. |
| 5,718,692 A | 2/1998 | Schon et al. |
| 5,728,064 A | 3/1998 | Burns et al. |
| 5,749,889 A | 5/1998 | Bacich et al. |
| 5,800,384 A | 9/1998 | Russell et al. |
| 5,800,414 A | 9/1998 | Cazal |
| 5,807,311 A | 9/1998 | Palestrant |
| 5,810,776 A | 9/1998 | Bacich et al. |
| 5,827,243 A | 10/1998 | Palestrant |
| 5,879,324 A | 3/1999 | Hoffmann |
| 6,312,374 B1 * | 11/2001 | von Hoffmann ................ 600/3 |

FOREIGN PATENT DOCUMENTS

| | | |
|---|---|---|
| EP | 0 056 103 | 1/1985 |
| EP | 0249456 | 12/1987 |
| EP | 0 495 263 | 7/1992 |
| EP | 0 504 934 | 9/1992 |
| EP | 0515119 | 11/1992 |
| EP | 0 616 817 | 9/1994 |
| EP | 0738520 A1 | 4/1996 |
| EP | 0 490 459 | 2/1997 |
| WO | WO 91/08010 | 6/1991 |
| WO | 94/00176 | 1/1994 |
| WO | 95/35130 | 12/1995 |
| WO | 96/29111 | 9/1996 |
| WO | WO 98/23319 | 6/1998 |
| WO | WO 98/23320 | 6/1998 |
| WO | 98/24501 | 6/1998 |
| WO | 99/20326 A | 4/1999 |

\* cited by examiner

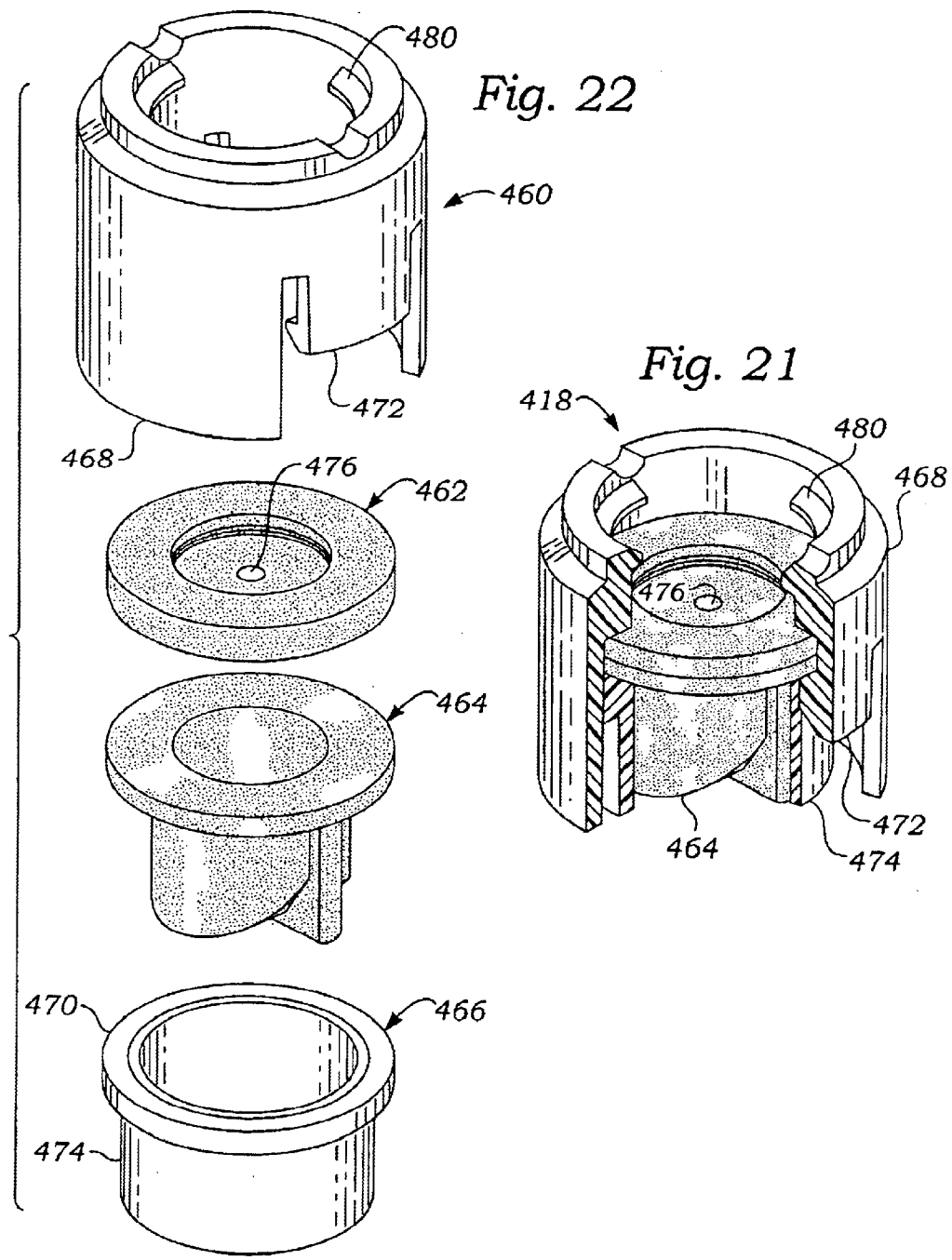

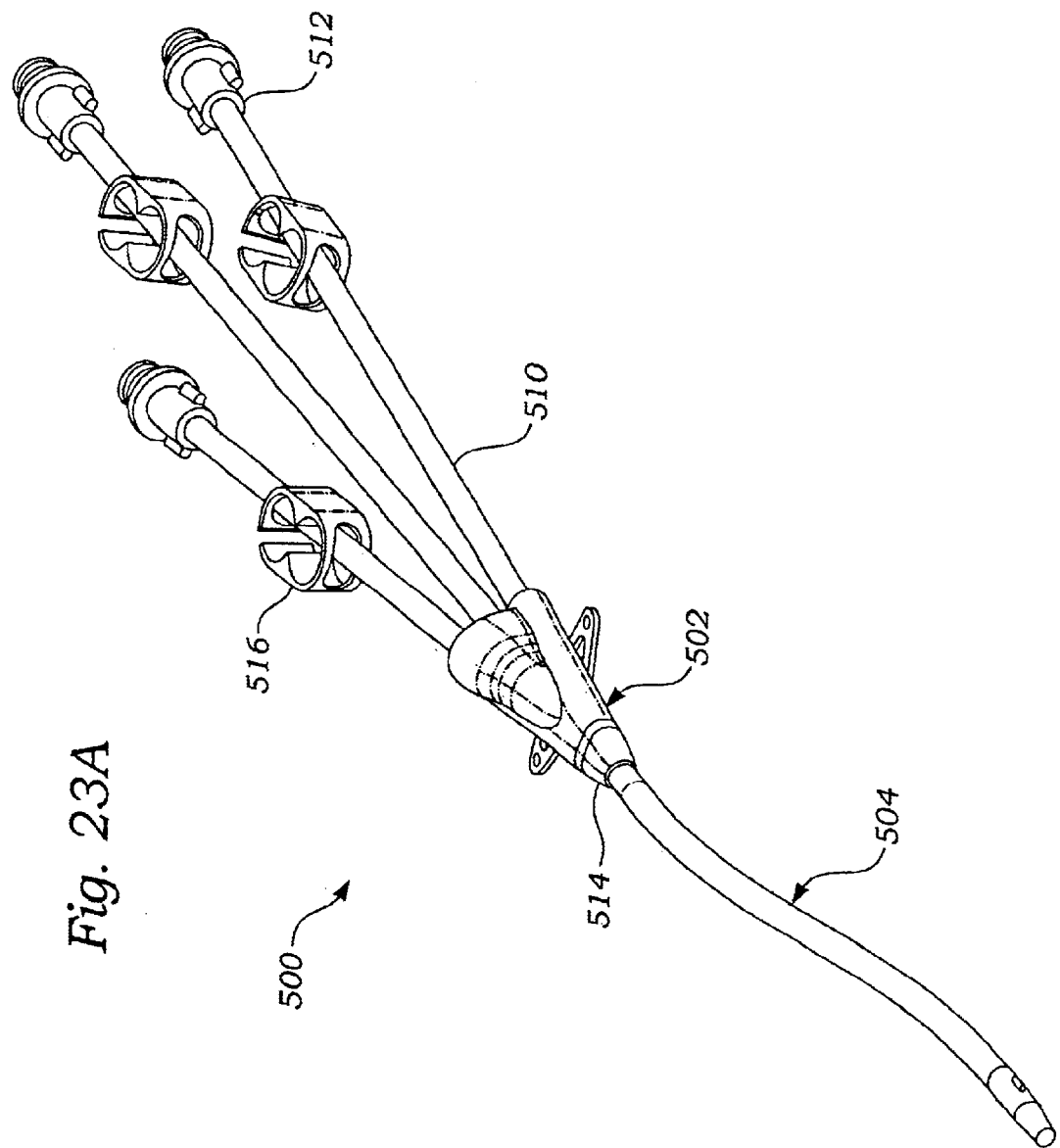

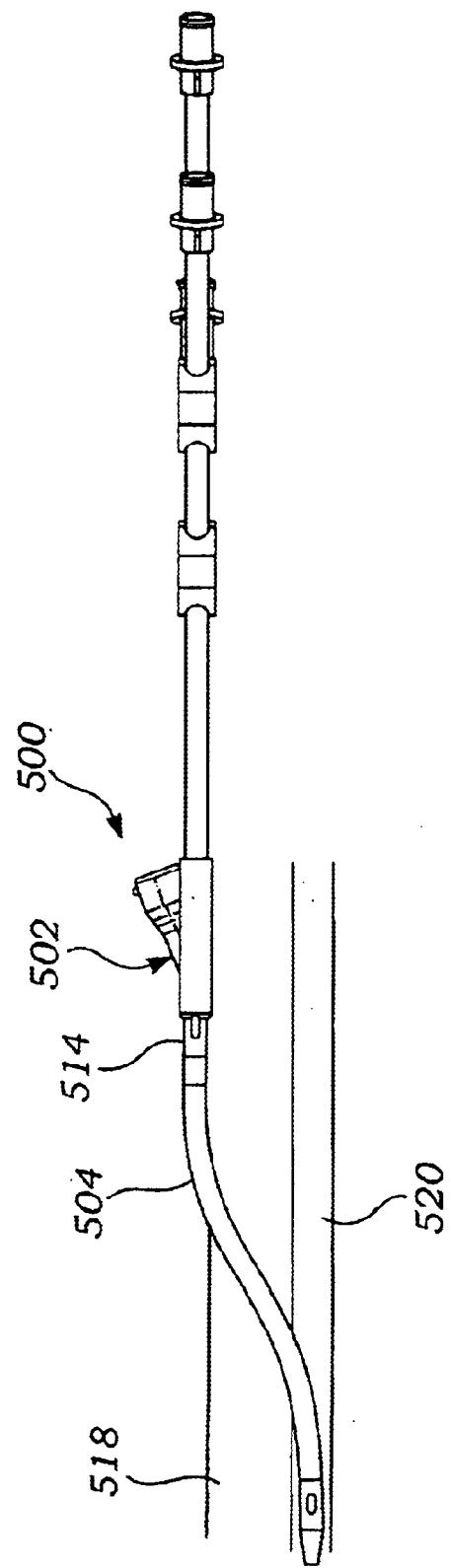

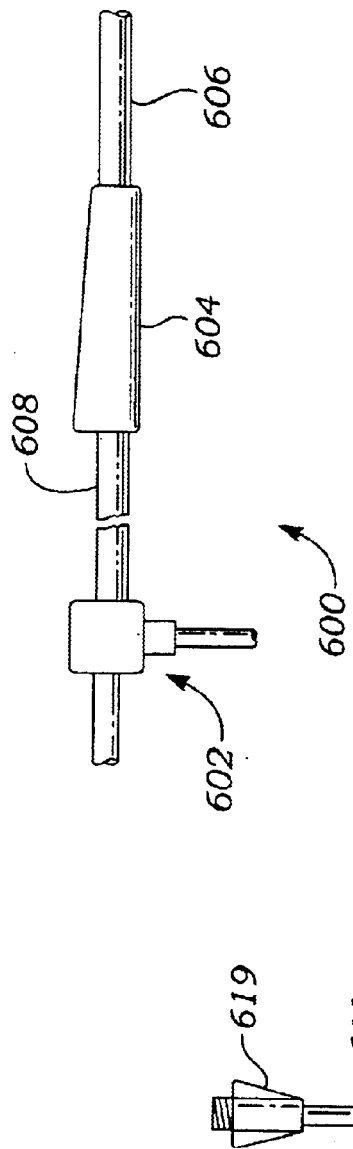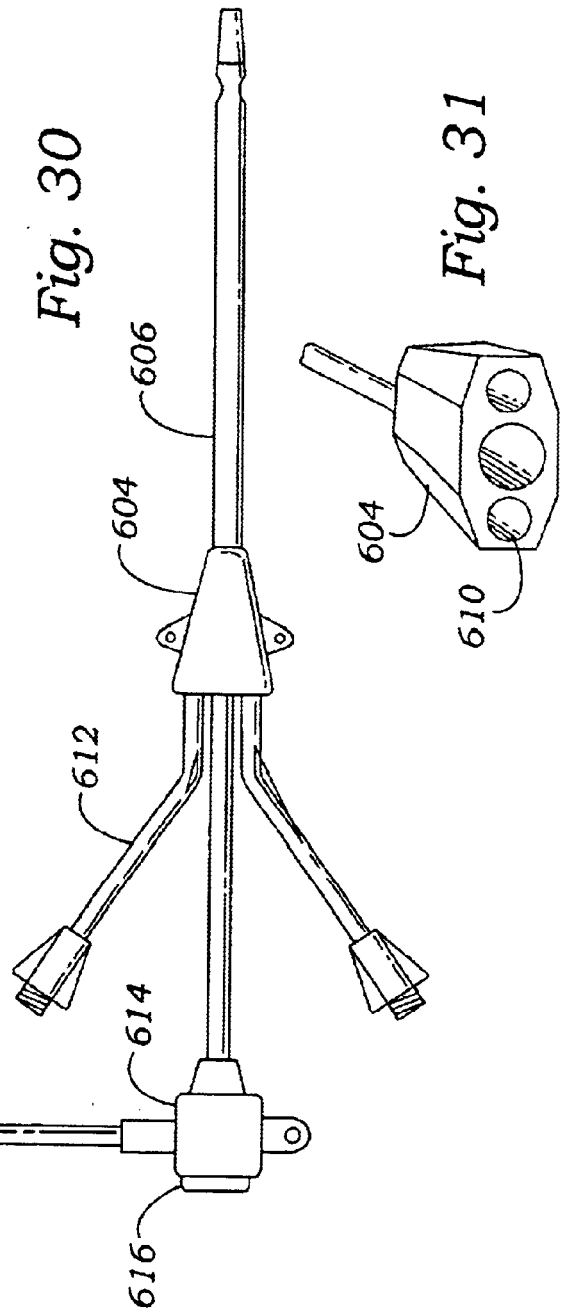

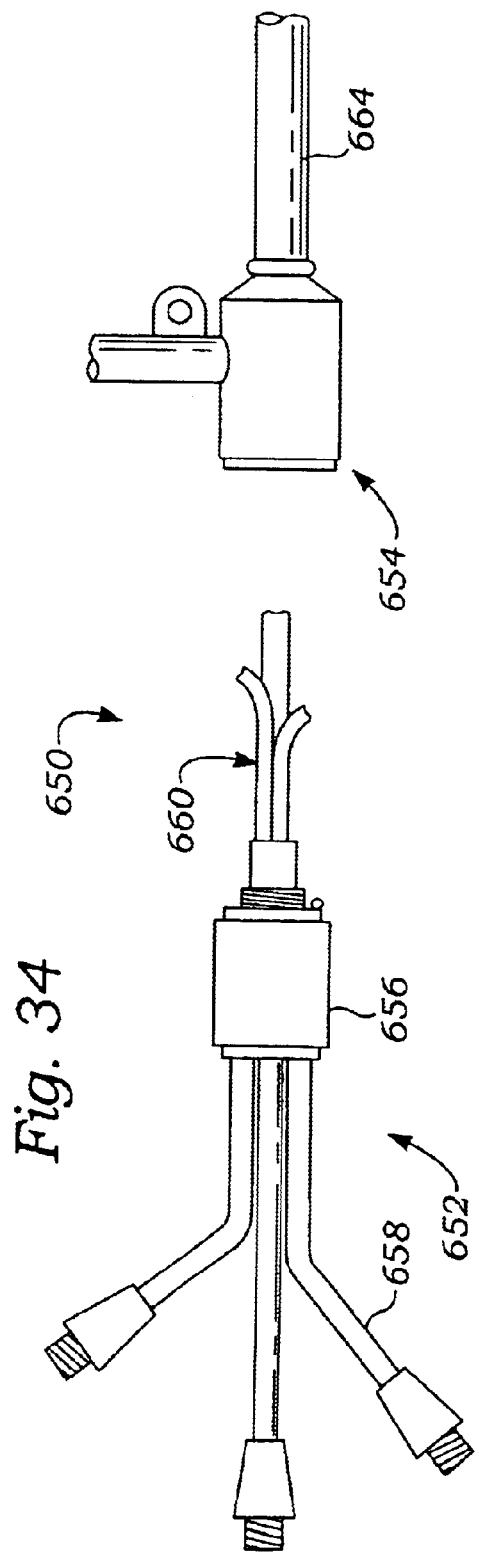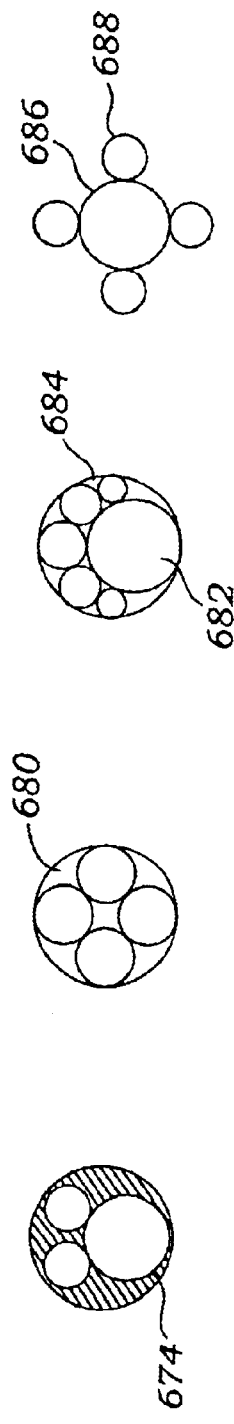

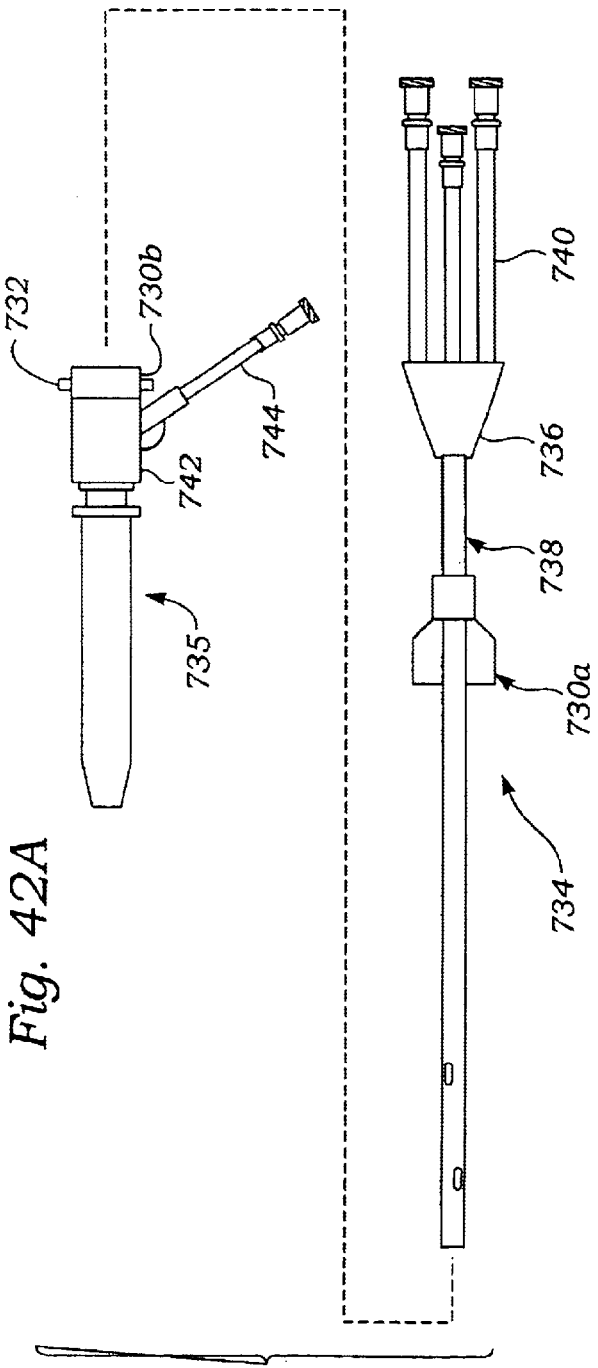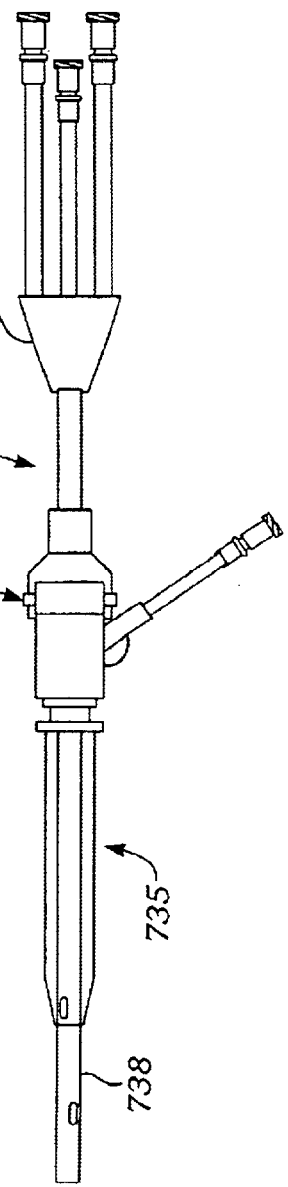
Fig. 42A
Fig. 42B

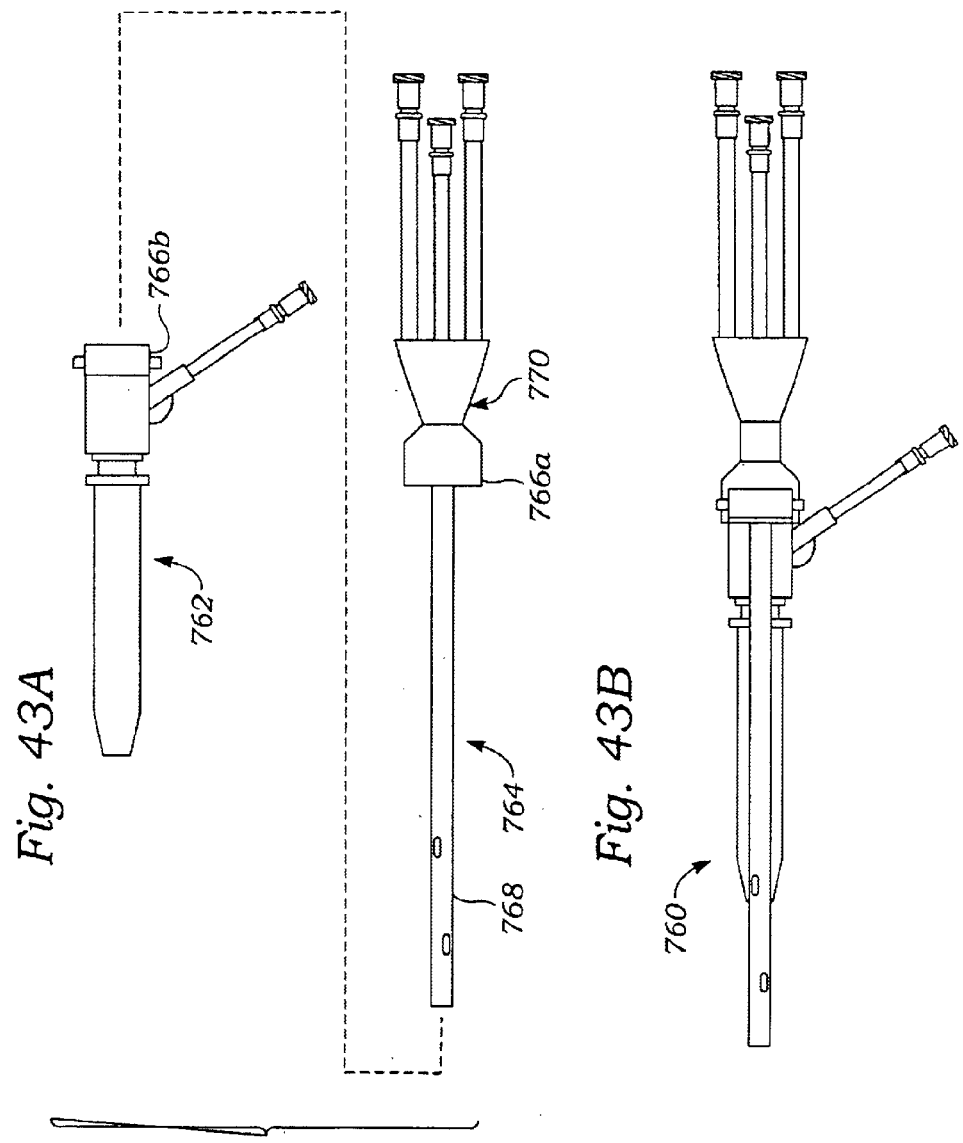

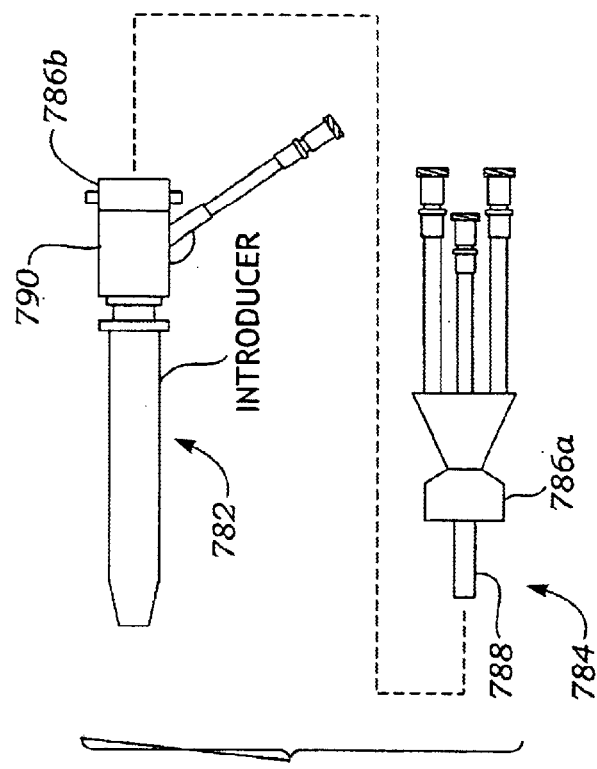
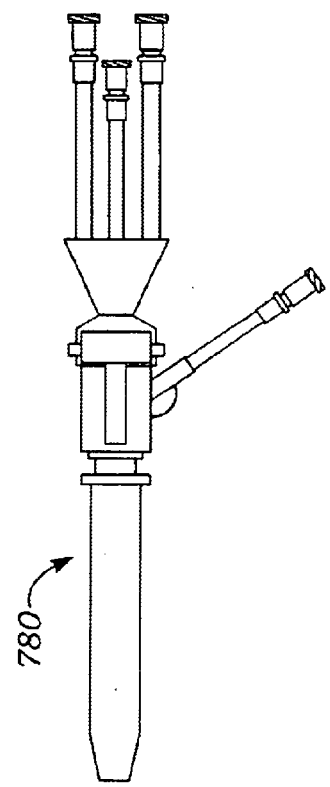
Fig. 44A
Fig. 44B

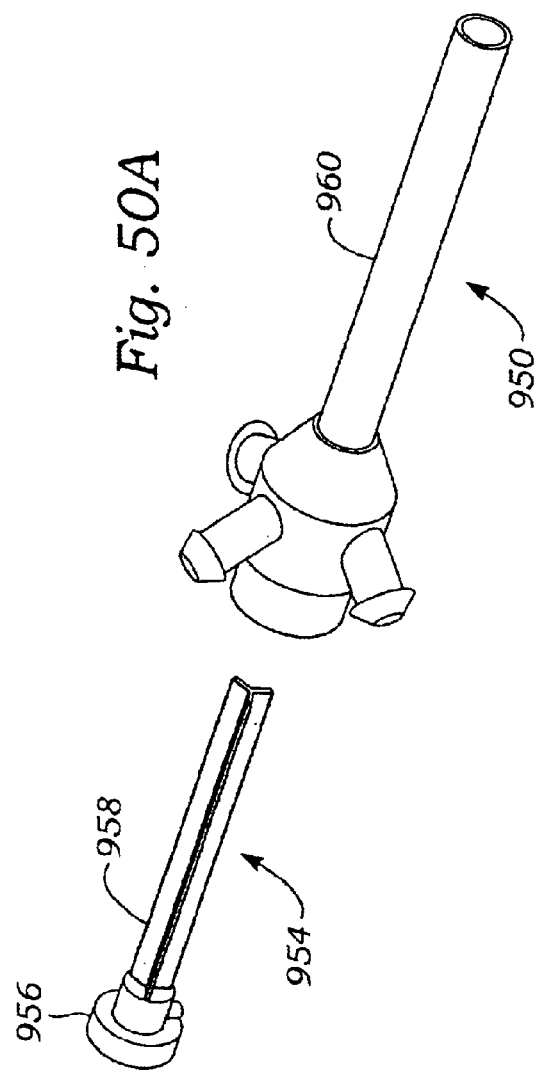
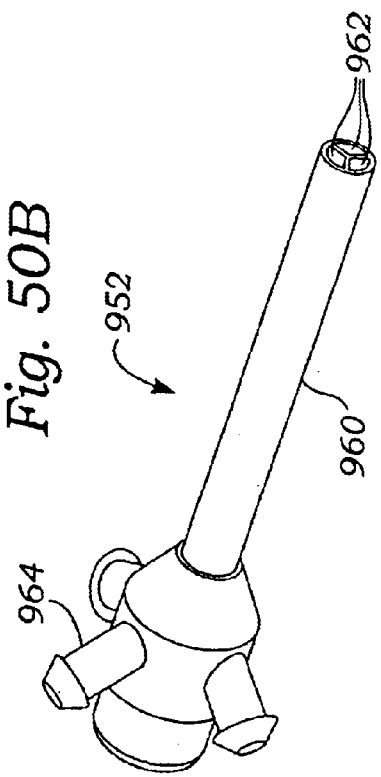

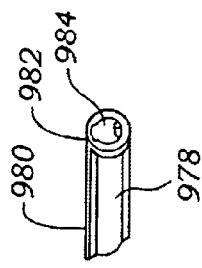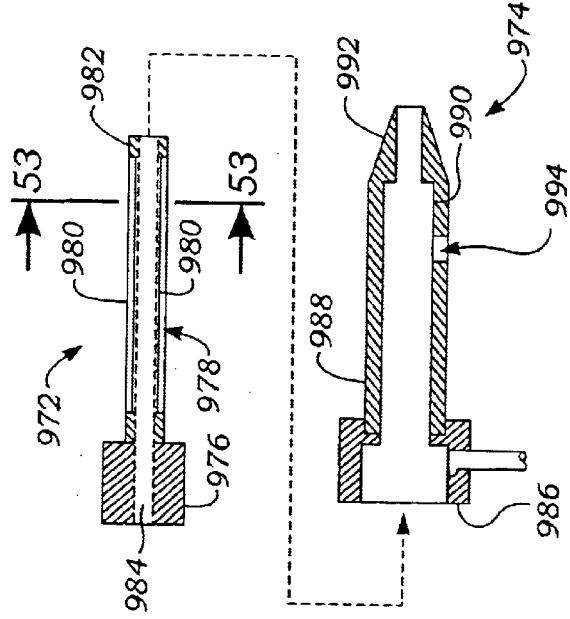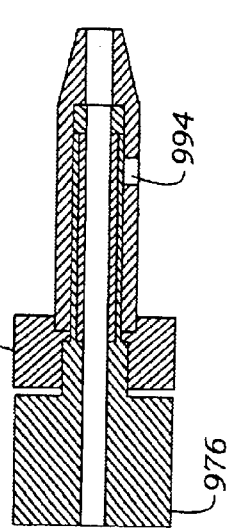

MULTIPLE LUMEN ACCESS DEVICE

RELATED APPLICATIONS

The present application is a continuation-in-part of U.S. application Ser. No. 08/953,105, filed Oct. 17, 1997 now abandoned, which is a continuation-in-part of U.S. application Ser. No. 08/756,763, filed Nov. 26, 1996 under the same title, abandoned. The entire contents of both of these prior applications are hereby incorporated by reference.

BACKGROUND OF THE INVENTION

1. Field of the Invention

The present invention relates generally to medical devices which are used to provide access into the human body. More particularly, the present invention is directed to access devices which provide a single, relatively long-term, entry port into the body. The entry port is used by doctors and other medical professionals to selectively introduce a variety of medical implements and fluids into the body and for in vivo diagnostic testing and other treatment protocols.

2. Description of Related Art

A wide variety of medical devices have been developed in recent years for providing access into the human blood stream. These devices have traditionally been divided into two different groups based on their function and purpose. The first group of devices includes catheters which are designed to introduce therapeutic and/or diagnostic fluids into the blood stream. The second group includes devices commonly referred to as "introducers" which are designed to provide an intermediate term access port into the body through which various medical implements may be passed for therapeutic and/or diagnostic purposes. As a generalization, catheters are longer and more flexible than introducers.

Central venous catheters are relatively long tubular devices which have tapered distal tips which are designed for entry into central veins to provide a dedicated route of fluid infusion into the body. The original venous catheters were single lumen devices which provided the ability to infuse a single liquid into the vein at one time. Multiple lumen catheters have since been developed which allow simultaneous introduction of two or more liquids into the vein. The central venous pressure catheter is a type of common multiple lumen catheter which allows the simultaneous introduction and withdrawal of fluids as well as the capability of monitoring blood pressure and other vital parameters. The portion of the catheter which remains outside of the body has been continually refined and redesigned to provide a low profile which increases comfort and reduces the awkwardness associated with a dedicated tube exiting the body.

Introducers are substantially different from catheters in both design and purpose. An introducer is an access device which is intended to provide a dedicated access port into the body. Catheters, on the other hand, are intended to be used to infuse or withdraw fluids from the body. Introducers typically include a relatively short lumen through which various medical implements, including catheters, can be selectively introduced and removed from the body. An important feature of any introducer is the valve assembly. The valve assembly provides a constant seal between the blood stream and the in vitro environment as medical implements are introduced and withdrawn from the body. The valve assembly is typically located outside of the body at the proximal end of the introducer. As a result, the proximal end of introducers has tended to be relatively bulky.

In addition to a valve assembly, many introducers include a side arm at the proximal end. The side arm is connected to the lumen so that fluids can be introduced into the body simultaneously with the medical device. The introducer lumen is considered to be a "shared" lumen in that the lumen provides a common conduit for both medical implements and fluid pharmaceuticals or diagnostics.

The currently available introducers and other access devices are well-suited for their intended purpose. However, new medical treatments and diagnostic procedures are continually being developed which require more versatile access into the body. For example, organ transplant procedures and cardiac angioplasty require the introduction of complex combinations of medical implements and diagnostic/therapeutic fluids into the body. Many of the presently available access devices are not well-suited for these relatively complex procedures. As a result, multiple access devices are required which must be located at multiple access sites necessitating multiple entry punctures. Accordingly, there is a continuing need to provide improved access devices that have additional capabilities which increase their versatility and usefulness for the increasing variety of invasive treatments and procedures.

SUMMARY OF THE INVENTION

In accordance with the present invention, an improved access device is provided which is designed to provide selective introduction of medical implements into the body while simultaneously providing auxiliary access through dedicated multiple lumens. The present invention is an improvement over existing introducers and other access devices in that multiple lumen access is provided through the introducer in addition to the shared lumen which is used for both medical implements and fluid pharmaceuticals or diagnostics. As an advantage, the improved access device reduces the number of devices required to introduce multiple implements and fluids into the body during complex surgical and diagnostic procedures.

The present invention desirably includes a multiple lumen access system for use in providing an entry port into the human body for selectively introducing medical implements therethrough and for providing simultaneous auxiliary access into the body. The system includes a multiple lumen access device comprising an outer tube which has a distal end for introduction into the body and a cross-sectional area. A device lumen through which medical implements may be passed is defined within the cross-sectional area of the outer tube, the device lumen having a distal end and a proximal end. At least one auxiliary lumen is defined within the cross-sectional area and separately from the device lumen, the auxiliary lumen having a distal end and proximal end. Finally, a device lumen valve is associated with the proximal end of the device lumen to provide sealing of the device lumen when medical implements are both present and absent from the device lumen. Such device lumen valve may be separate and detachable or it may be integral with the system.

A multiple lumen access system according to the present invention may also include a junction housing having a proximal end and a distal end to which the proximal end of the outer tube connects. The junction housing includes a main channel in fluid communication with the device lumen and at least one auxiliary channel in fluid communication with the at least one auxiliary lumen, the main channel and auxiliary channel(s) diverging from the outer tube to be non-intersecting in the junction housing.

In one embodiment, the device lumen valve is provided as a part of the junction housing and is in fluid communication with the main channel. A device channel may be formed in the junction housing at an angle with the main channel and terminating at an internal end in fluid communication with the main channel. The device lumen valve may be positioned at an external end of the device channel so that medical devices may be inserted therethrough and enter the main channel at an angle. The main channel desirably may continue from the distal end of the junction housing past the device lumen to an opening in the junction housing enabling introduction of fluids therethrough to the main channel. In one embodiment, the device lumen valve is molded separately from the junction housing of a material more rigid than the junction housing and is assembled with the multiple lumen access device by insertion in a cavity formed in the junction housing.

In an alternative embodiment, the main channel and auxiliary channel(s) of the junction housing may be oriented substantially coplanar so that the junction housing is substantially flat, the system further including an extension tube extending from the proximal end of the junction housing and in fluid communication with the main channel wherein the device lumen valve is connected to the extension tube to therefore be in fluid communication with the main channel. A side port in the device lumen valve may be provided enabling infusion of fluids to the extension tube and main channel. Furthermore, mating threaded connectors may be included between the device lumen valve and the extension tube enabling easy removal of the device lumen valve. Any appropriate connector, for example a luer connector, may be provided on the device lumen valve, and the system may also include an infusion syringe having a mating luer connector.

Further, in one embodiment, a multiple lumen access device may be provided with a multi-lumen sheath, a junction housing coupled to the multi-lumen sheath and a strain relief insert coupled to the junction housing. The strain relief insert is formed of a soft bendable material capable of flexing to prevent multi-lumen sheath from kinking at the sheath/junction housing coupling. In further embodiment, the multiple lumen access device is formed by coupling a single lumen catheter to a junction housing having a main channel and at least one auxiliary channel through a multi-function adapter.

In another embodiment, the present invention is directed to a multiple lumen access device including an outer tube which has a distal end for introduction into the body and a proximal end which remains outside of the body. The outer tube may have an exterior surface and an interior surface, the interior surface defining an access passageway which has a cross-sectional area which may vary at different locations between the distal and proximal ends of the outer tube. One or more inner walls are located within the access passageway. The inner wall may form an inner tube that surrounds a device lumen through which medical implements may be inserted into the body. At least one auxiliary lumen is located between the exterior surface of the inner wall and the interior surface of the outer tube.

As another feature of the present invention, two or more auxiliary passageways defined by the interior surface of the outer tube and the exterior surface of the inner walls. The provision of two or more auxiliary passageways allows introduction of additional diagnostics or pharmaceutical liquids simultaneously with introduction of a medical implement through the device lumen. Embodiments of the present invention are also described wherein a single auxiliary lumen is provided.

As a further desirable feature of the present invention the inner walls are sufficiently flexible to be movable from a relaxed position to expanded or contracted positions. The device lumen has a first cross-sectional area in the relaxed position, and in the expanded or contracted positions has cross-sectional areas which are greater than or less than the first cross-sectional area, and less than the cross-sectional area of the access passageway. The flexibility of the inner walls is advantageous in that it allows the insertion of a variety of medical implements having different cross-sectional areas. This flexibility allows the cross-sectional areas and resultant potential fluid flow rate for the auxiliary lumens and the device lumen to be controlled as desired and maximized within the confines of the access passageway.

As an additional feature of the present invention, spacer ribs are provided, for example, on the interior surface of the outer tube. The spacer ribs are located within the auxiliary lumens to prevent complete closure of the lumens during insertion of relatively large medical implements into the device lumen. The spacer ribs located on the surface of the inner wall insure that there is a passageway around devices located within the device lumen.

An alternative multiple lumen access device of the present invention comprises a tubular single lumen sheath having at least one infusion port and an elongated implement sized to fit coaxially within the single lumen sheath and form multiple independent lumens, and when at least one of the lumens is in fluid communication with the infusion port. The elongated implement may be formed from a sufficiently flexible material so that at least one lumen formed by the sheath and the implement has flexible walls movable from a relaxed to a flexed positions. Another alternative multiple lumen access device comprises a multi-lumen catheter having a main lumen tube, at least one side lumen tube connected in a side-by-side fashion with the main lumen tube and being peelable from the main lumen to form sidearms, and a hub connected to the main lumen tube and side lumen tube for fluid delivery or passage of a medical device therethrough.

The present invention is also directed to a method for introducing medical devices into the body through a single entry port while allowing simultaneous introduction of other devices, implements or fluids through the use of the multiple lumen access device of the present invention. In one embodiment, the method includes the steps of providing a multiple lumen access device in accordance with the present invention having at least one flexible wall; introducing the multiple lumen access device into the body with the distal ends of the device lumen and the auxiliary lumen being positioned within a vasculature of the body; and flowing a medical solution through the auxiliary lumen to move the flexible wall from the relaxed position to a flexed position.

In another embodiment, the method includes the steps of providing a tubular single lumen sheath having proximal and distal ends, at least one infusion port being provided on the proximal end of the sheath; providing an elongated implement sized to fit coaxially within the single lumen sheath, at least one of the lumens being in fluid communication with the infusion port; inserting the elongated implement into the single lumen sheath to form multiple independent lumens therein; and flowing a medical solution through one or more of the multiple independent lumens.

The above-described and many other features and attendant advantages of the present invention will become better understood by reference to the following detailed description when taken in conjunction with the accompanying drawings.

BRIEF DESCRIPTION OF THE DRAWINGS

FIG. 21 is a perspective assembled view of a valve insert used in the junction housing of FIG. 16.

FIG. 22 is an exploded perspective view of the valve insert of FIG. 21.

FIGS. 23A and 23B are two perspective views of a multiple lumen access device similar to that shown in FIG. 16.

FIG. 24 is an elevational view of the multiple lumen access device of FIGS. 23A/23B in place in the vasculature of a patient.

FIG. 29 is an elevational view of a multiple lumen access device in accordance with the present invention.

FIG. 30 is a plan view of the multiple lumen access device of FIG. 29 showing more details of an associated catheter system.

FIG. 31 is a perspective view of a proximal end of a low-profile junction housing of the device of FIG. 29.

FIG. 34 is a plan view of an alternative multiple lumen access having a multi-lumen infusion catheter interfacing with a single lumen introducer.

FIGS. 35A–35D are schematic sectional views of sheath/lumen configurations for use in the multi-lumen infusion catheter of FIG. 34.

FIG. 42A is an exploded view of a multiple lumen access device having an introducer connected to a multi-lumen catheter by an adjustable adapter.

FIG. 42B is an assembled view of the multiple lumen access device of FIG. 42A.

FIG. 43A is an exploded view of a multiple lumen access device having an introducer with infusion port connected to a multi-lumen catheter by an adapter.

FIG. 43B is an assembled view of the multiple lumen access device of FIG. 43A.

FIG. 44A is an exploded view of a multiple lumen access device having an introducer with infusion port connected to a triple lumen junction housing and obturator by an adapter.

FIG. 44B is an assembled view of the multiple lumen access device of FIG. 44A.

FIG. 50A is an exploded view of a multiple lumen access device with a multi-ribbed solid obturator telescopically fitting within an introducer with infusion ports.

FIG. 50B is an assembled view of the multiple lumen access device of FIG. 50A.

FIG. 51 is an exploded sectional view of a multiple lumen access device with a multi-ribbed hollow obturator telescopically fitting within a tapered introducer with an infusion port.

FIG. 52 is an assembled view of the multiple lumen access device of FIG. 51.

FIG. 53 is a sectional view of the obturator seen in FIG. 51 taken along line 53—53.

FIG. 54 is a perspective view of a portion of the obturator seen in FIG. 51.

DESCRIPTION OF THE PREFERRED EMBODIMENTS

Figure 1:
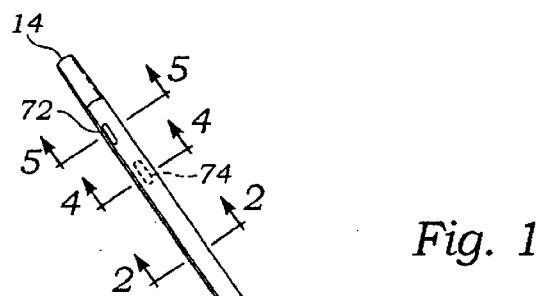
FIG. 1 is a perspective view of an exemplary preferred multiple lumen access device in accordance with the present invention.

An exemplary multiple lumen access device (MLAD) in accordance with the present invention is shown generally at 10 in FIGS. 1–5. The device 10 includes an outer tube 12 which has a distal end 14 and a proximal end 16. As best shown in FIGS. 2–5, the outer tube 12 has an exterior surface 18 and an interior surface 20. The interior surface 20 defines an access passageway or lumen 22 which has a cross-sectional area that may vary at different locations between the distal 14 and proximal 16 ends of the outer tube 12. Typically, the outer tube 12 may be tapered at the distal end 14, if desired. As a result of the tapering of the outer tube 12, the cross-sectional area will decrease accordingly.

Figure 2:
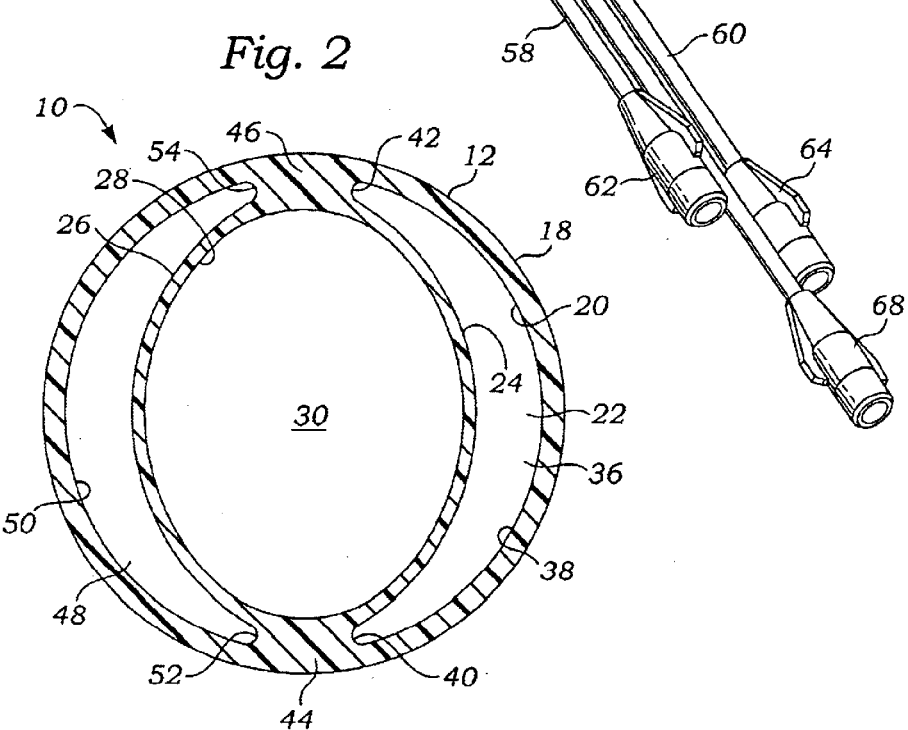
FIG. 2 is a sectional view of FIG. 1 taken in the 2—2 plane of FIG. 1.

In accordance with the present invention, an inner tube 24 is located within the access passageway 22. The inner tube 24 has a distal end and a proximal end which correspond to the distal end 14 and proximal end 16 of the outer tube 12. As illustrated in FIG. 2, the inner tube 24 is formed by a wall surrounding a device lumen 30, the wall having an exterior surface 26 and an interior surface 28. The interior surface 28 defines a device lumen 30 through which medical implements (such as catheters 32 and 34 shown in FIGS. 3A and 3B, respectively) may be inserted into the body. Catheter 34 is also shown in position within the device lumen 30 in FIGS. 4 and 5.

Two auxiliary lumens 36 and 48 are located between the exterior surface 26 of the inner tube 24 and the interior surface 20 of the outer tube 12. The auxiliary lumens 36 and 48 each have a distal end and a proximal end which correspond generally to the distal and proximal ends of the outer tube 12 and inner tube 24. In this particular preferred embodiment, the surfaces which define the auxiliary lumens 36 and 48 correspond to portions of the interior surface of the outer tube and exterior surface of the inner tube. Specifically, auxiliary lumen 36 is defined or bordered by an interior surface 38 which corresponds to the interior surface 20 of the outer tube 12 and the exterior surface 26 of the inner tube 24. Further, the auxiliary lumen 36 is defined by separation surfaces 40 and 42 which are formed by separation barriers 44 and 46, respectively.

A second auxiliary lumen 48 is also formed or defined by the interior surface 20 of the outer tube 12 and the exterior surface 26 of the inner tube 24. Accordingly, the interior surface 50 which defines the second auxiliary lumen 48 corresponds to these surfaces. In addition, the auxiliary lumen 48 is bordered by separation surfaces 52 and 54 formed by separation barriers 44 and 46, respectively.

Referring to FIG. 1, the multiple lumen access device 10 includes a junction housing 56. The junction housing 56 is connected to the proximal end 16 of the access lumen 12. The housing 56 includes infusion tubes 58 and 60 which are connected through the housing 56 to auxiliary lumens 36 and 48, respectively. The infusion tubes 58 and 60 include luer connectors 62 and 64. Other conventional connection devices may be used. A third infusion tube 66 is connected via the housing 56 to the device lumen 30 in order to provide a route for infusion of liquid into the device lumen 30. It should be noted that the infusion tube 66 is not connected to the junction housing 56 at a right angle as is typically done in conventional introducer-type devices. Instead, the infusion tube 66 extends from the housing 56 parallel to the other two infusion tubes 58 and 60. This parallel orientation of the tubes 58, 60 and 66 allows housing 56 to be a low profile body which reduces the bulkiness of the proximal end of the device and increases its wearing comfort. A conventional locking device, such as luer lock 68 is also provided at the proximal end of the infusion tube 66.

The housing 56 includes a valve 70 through which various medical implements are inserted into the device lumen 30. Valve 70 includes a valve or gasket assembly which is designed to provide sealing of the device lumen 30 when medical implements are both present and absent from the device lumen 30. Any of the known gasket arrangements and valve mechanisms used to provide sealing of introducers and related medical implement access devices are suitable. The multiple lumen access device 10 is designed for use in combination with providing access to either the arterial or venous sides of the bloodstream.

An opening 72 (see FIG. 1 and FIG. 5) is provided towards the distal end of outer tube 12. The opening 72 is provided to allow exit of fluid from auxiliary lumen 48 which has been introduced through infusion tube 58. Likewise, an opening 74 (shown in phantom in FIG. 1 and also shown in FIG. 4) is provided for allowing the fluid introduced through infusion tube 60 to exit auxiliary lumen 36 at the distal end of the outer tube 12.

Figure 4:
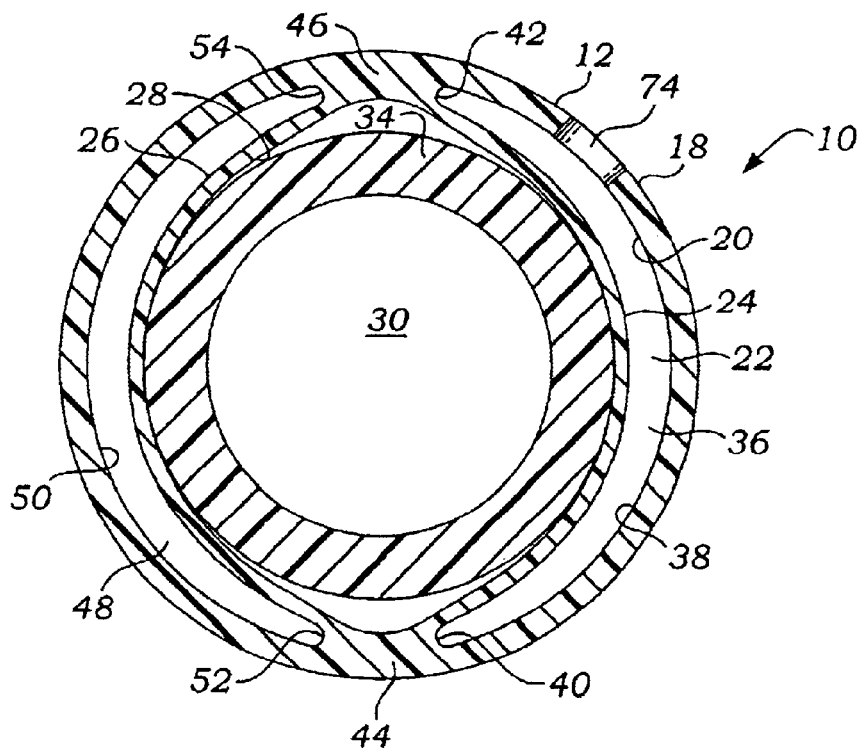
FIG. 4 is a sectional view of FIG. 1 taken in the 4—4 plane.
Figure 5:
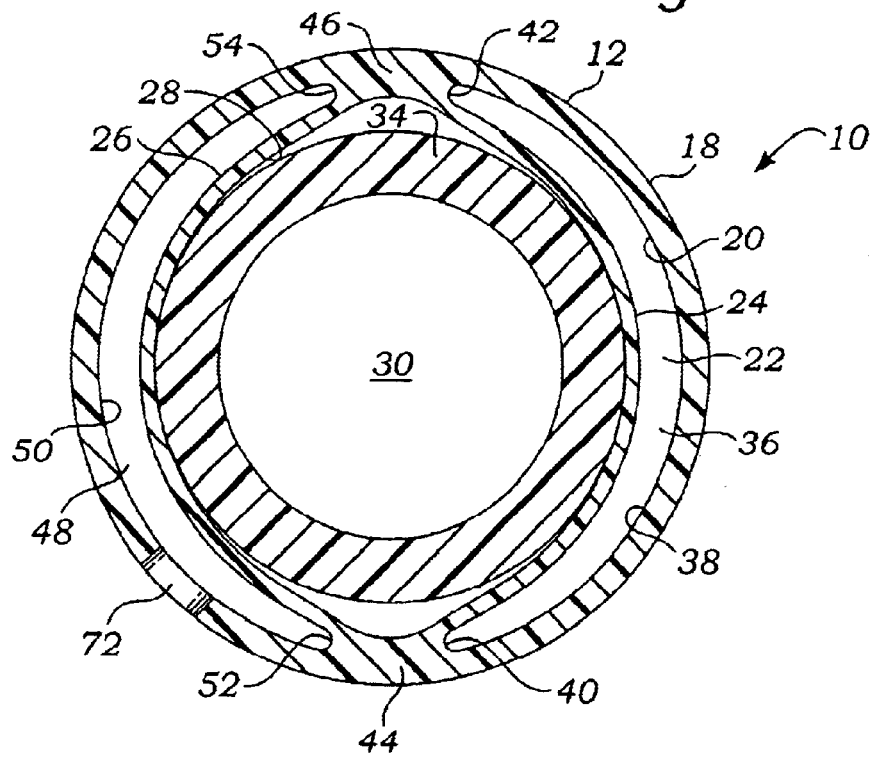
FIG. 5 is a sectional view of FIG. 1 taken in the 5—5 plane.

As illustrated in FIGS. 1, 4 and 5, the openings 72 and 74 are preferably sized to avoid restricting fluid flow through the respective auxiliary lumens. Therefore, it is preferred that the openings 72 and 74 are each sized sufficiently large to be equal or greater than the maximum distended/ expanded cross-sectional area of the corresponding auxiliary lumens 36 and 48. Of course, this same principle applies with regard to any number of auxiliary lumens each having a variable cross-section. When either auxiliary lumen 36, 48 is under pressure and no device is present in the device lumen 30, the auxiliary lumen cross-section increases in diameter. In one preferred embodiment, the auxiliary lumen increases, for example, from approximately 15 gauge to about 12 gauge, while in another embodiment the auxiliary lumen increases from approximately 18 gauge to about 14 gauge. Therefore, the openings 72 and 74 are each sized to be equivalent to or greater than 12 gauge or 14 gauge, respectively, to avoid restricting fluid flow through the respective auxiliary lumen. When other cross-section diameters of the auxiliary lumens are used, the size of the openings, such as 72 and 74, are preferably sized accordingly.

Figure 3A:
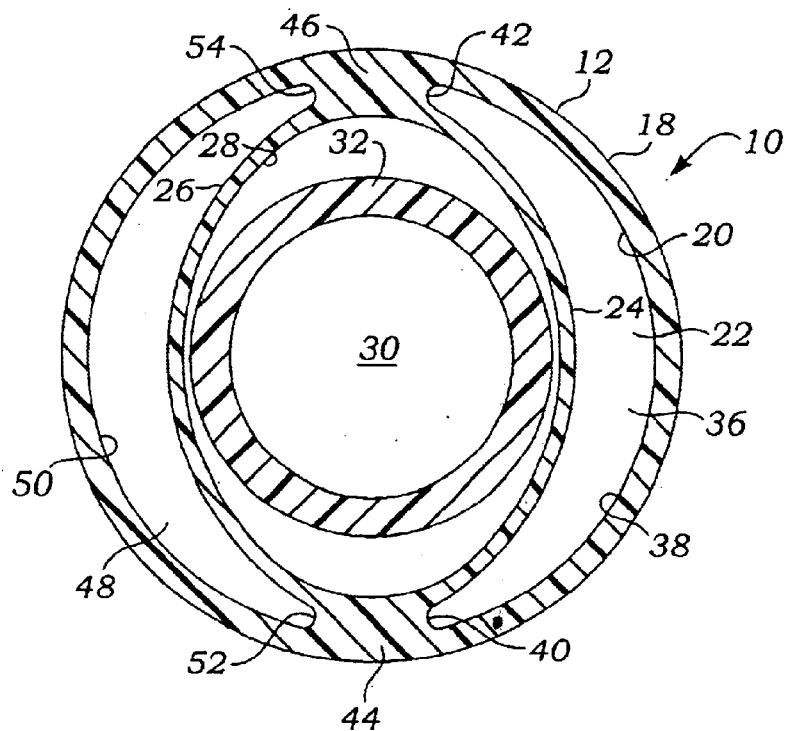
FIG. 3A is a sectional view taken in the same 2—2 plane of FIG. 1 which shows a relatively small diameter medical device located within the device lumen.
Figure 3B:
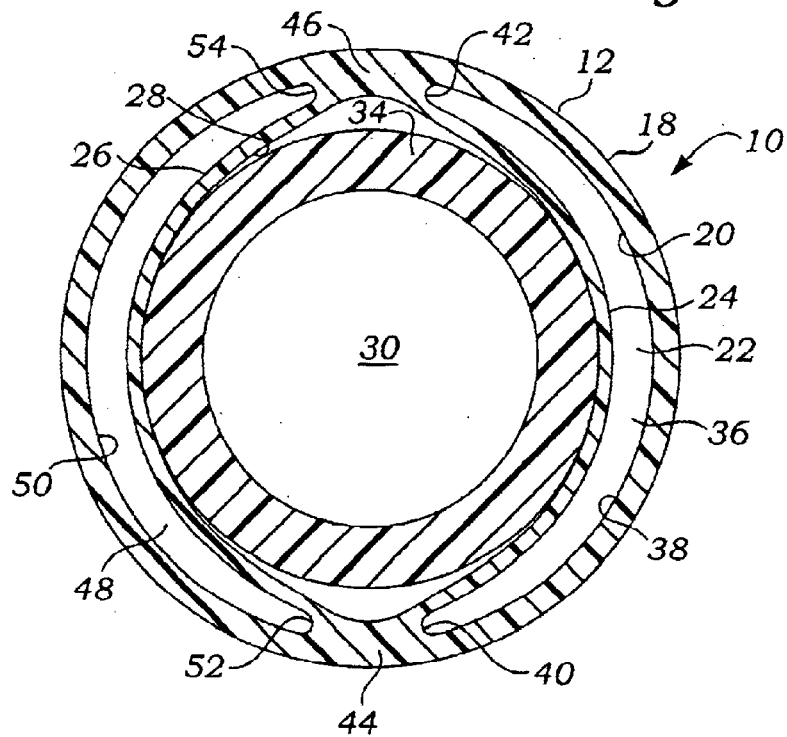
FIG. 3B is a sectional view taken in the same 2—2 plane of FIG. 1 showing a relatively large diameter medical implement located within the device lumen.

In this exemplary embodiment of the present invention, the inner tube 24 must be sufficiently flexible to be stretchable between a relaxed position as shown in FIG. 3A and various expanded positions as exemplified in FIG. 3B. In FIG. 3A, a catheter 32 having a diameter of 1.3 millimeter (4 French) is shown inserted within the device lumen 30. The inner tube 24 is in a relaxed position where the cross-sectional area of the device lumen 30 is approximately 2 square millimeters. The relaxed cross-sectional area of the device lumen 30 will preferably range from 1 to 3 square millimeters. Larger diameters are possible, if desired. It is preferred, but not required, that inner tube 24 have a circular or elliptical cross-section.

As shown in FIG. 3B, a larger diameter catheter 34 has been inserted into the device lumen 30. The inner wall 24 is made from sufficiently resilient material and is sufficiently sized so that it can expand to the diameter shown which is approximately 3 millimeter (9 French). The maximum diameters to which the inner tube 24 can be expanded is limited by the diameter of the outer tube 12. The inner tube 24 may be flexed inward, if desired, by applying fluid pressure through one or both auxiliary lumens 36 and 48. Typically, the cross-sectional area of the device lumen 30 when the inner tube 24 is in its maximum expanded state will range from 5 to 9 square millimeters. Larger diameters are possible, if desired. Preferably, the inner tube 24 will be sufficiently flexible so that it can be expanded completely outward against the interior surface 20 of the outer tube 12. In the fully expanded state, the auxiliary lumens 36 and 48 will have substantially reduced cross-sectional areas. However, it is preferred that the auxiliary lumens 36 and 48 not be entirely closed. It is desirable to leave some opening through these two auxiliary lumens 36 and 48 at all times to allow flushing fluids to be passed through the lumens in order to prevent the formation of blood clots or other problems associated with a completely collapsed lumen.

Preferably, the inner tube 24 is sufficiently flexible to be stretched to expanded positions wherein the cross-sectional area of the device lumen 30 in the expanded state is up to 85 percent of the cross-sectional area of the access lumen 22. This allows for continual auxiliary fluid introduction through auxiliary lumens 36 and 48. Further, it is preferred that in the relaxed position as shown in FIG. 3, that the device lumen 30 have a cross-sectional area which is not less than 35 percent of the cross-sectional area of the access lumen 22.

In accordance with the present invention, the inner tube 24 is preferably connected to the outer tube 12 at separation barriers 44 and 46 in order to divide the access lumen 22 into a three-chamber lumen, i.e. the central device lumen 30 and two auxiliary lumens 36 and 48. In order to achieve the desired flexibility of the device lumen 30, it is preferred that a relatively elastic material be utilized. Suitable elastic materials include, but are not limited to, polyvinylchloride, polyurethane, polyethylene, nylon, silicone, fluoropolymers and polypropylene. Further, in order to achieve the desired variation in lumen cross-sectional areas, the thickness and durometer of the inner tube walls 24 must be carefully matched to the particular material being utilized. For less flexible materials, the wall thicknesses must be correspondingly reduced in order to achieve the desired flexibility limits. The inner tube 24 should be sufficiently flexible so that it can be expanded to diameters which are at least as large as the outer tube 12.

Figure 6:
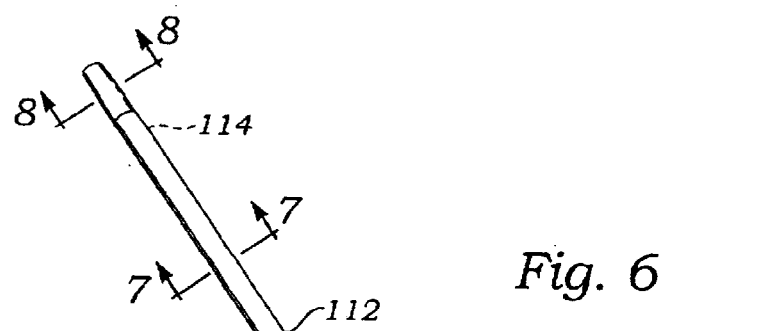
FIG. 6 is a perspective view of a preferred exemplary embodiment in accordance with the present invention.
Figure 7:
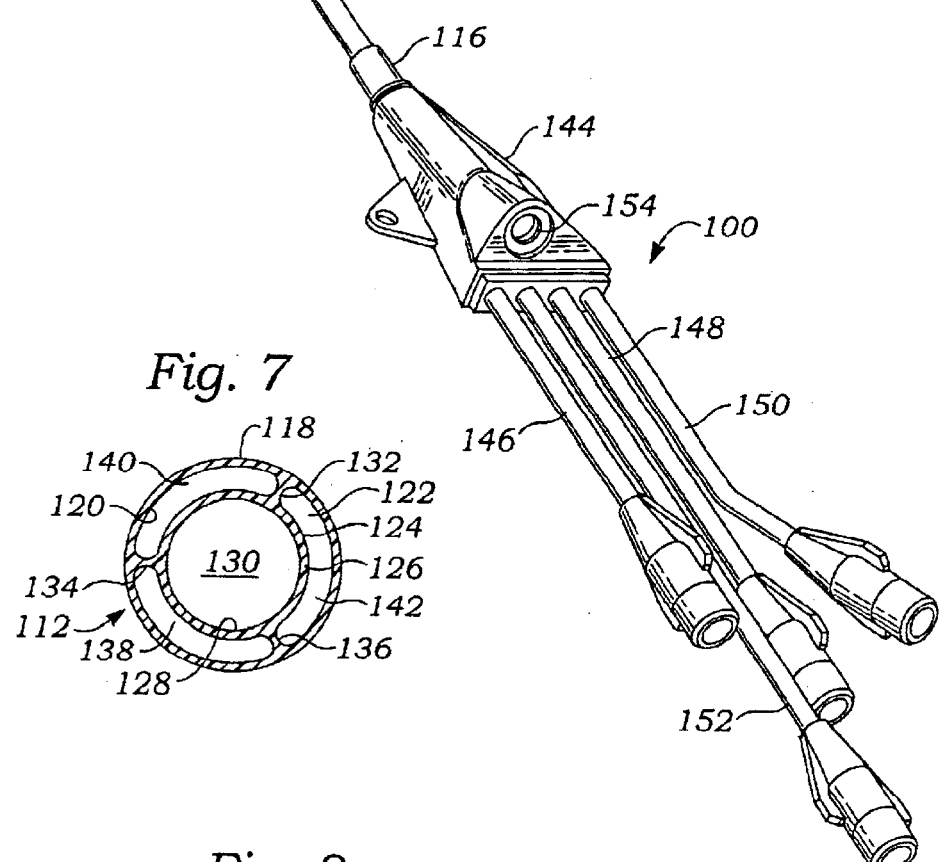
FIG. 7 is a sectional view of FIG. 6 taken in the 7—7 plane.
Figure 8:
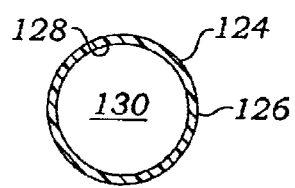
FIG. 8 is a sectional view of FIG. 6 taken in the 8—8 plane.

Another exemplary embodiment in accordance with the present invention is shown generally at 100 in FIG. 6. The access device 100 is similar to the previous preferred embodiments in that it includes an outer tube 112 having a distal end 114 and a proximal end 116. As best shown in FIGS. 7 and 8, the outer tube 112 has an exterior surface 118 and an interior surface 120. The interior surface defines an access passageway 122 in which an inner tube 124 is located. The inner tube 124 includes an exterior surface 126 and an interior surface 128. The interior surface 128 of the inner tube 124 defines a device lumen 130 through which medical implements, such as a catheter, may be inserted. The access device 100 includes three separation barriers 132, 134 and 136 which, in combination with the interior surface of the outer tube 120 and exterior surface of the inner tube 126, form three auxiliary lumens 138, 140 and 142. The multiple lumen access device 100 includes the same type of junction housing 144 which was described in the previously-described preferred embodiment (FIGS. 1–5), except that an additional infusion lumen is included to provide infusion of liquid into the additional auxiliary lumen. As shown in FIG. 6, infusion lumens 146, 148 and 150 are connected via junction housing 144 to auxiliary lumens 138, 140 and 142, respectively. A primary infusion lumen 152 is also provided for introducing fluids into the device lumen 130. Again, an access port 154 is provided with the appropriate gaskets and/or valving mechanism to allow introduction of catheters and other medical devices into the device lumen 130.

The inner tube 124 in this exemplary embodiment may or may not be made from flexible material. The inclusion of three separation barriers in this particular embodiment reduces the ability for flexible expansion and contraction of the inner tube 124. However, it is preferred that the material used to form the device lumen 124 and the separation barriers be more flexible than the exterior outer tube 112 in order to allow variations in the cross-sectional areas of the auxiliary lumens. Otherwise, the same materials and fabrication techniques which are used to fabricate the prior embodiments are also suitable for use in making the multiple lumen access device 100.

Figure 9:
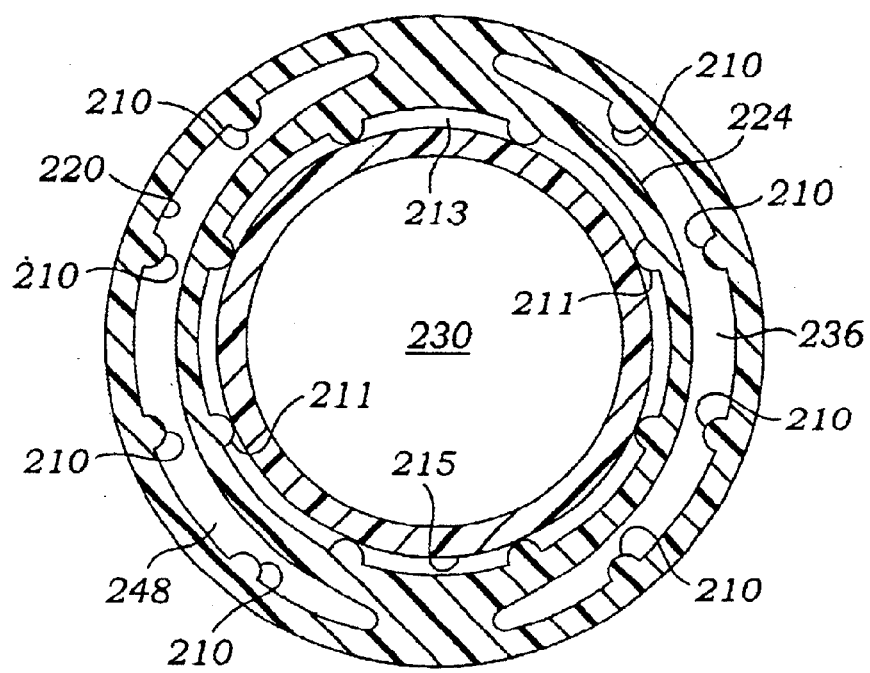
FIG. 9 is a sectional view of a preferred exemplary flexible inner wall showing the location of spacing ribs.

In a preferred embodiment, as shown in FIG. 9, spacer ribs 210 are provided on the interior surface 220 of the outer tube 212 to prevent the inner tube 224 from being expanded to a position which closes the auxiliary lumens 236 and 248. Spacer ribs 211 may also be provided to insure that a passageway 213 is maintained around a device 215 when it is located within device lumen 230. The ribs 210 are preferably located longitudinally along the entire length of the outer tube 212 where the inner tube 224 is also present. The particular cross-sectional shape of the spacer ribs 210 is not particularly important so long as they are relatively blunt and do not damage the inner tube 224 during contact therewith. The number and relative positioning of the spacer must be chosen to insure that complete closure of the auxiliary lumens 236 and 248 does not occur. For inner tubes 224 which are relatively flexible, the number and size of ribs may have to be increased. The ribs 210 shown in FIG. 9 are an example of a preferred configuration. The number, shape, size and position of the ribs 210 may be varied as required in order to prevent closure of the auxiliary lumens 236 and 248 as discussed above.

Although more than two auxiliary lumens may be included into the access device, it is preferred that two lumens be utilized. The use of two lumens is a preferred design for allowing uniform expansion of the inner tube 24 between the relaxed state as shown in FIG. 3A and an expanded state as shown in FIG. 3B.

Figure 10:
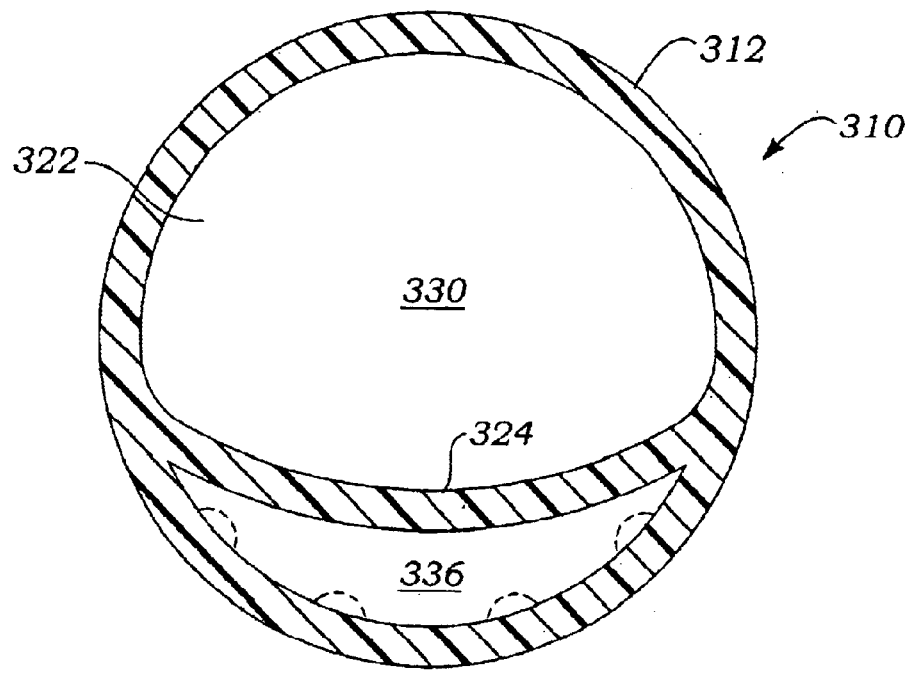
FIG. 10 is a sectional view of a preferred exemplary multiple lumen access device having a single auxiliary lumen.

Access devices which include one auxiliary lumen are also possible. The cross-section of an exemplary access lumen is shown at 310 in FIG. 10. The access lumen 310 includes an outer tube 312 which defines an access lumen 322. The access lumen 322 is divided into a device lumen 330 and an auxiliary lumen 336 by an inner flexible wall 324. The inner surface of the outer wall 312 preferably includes spacer ribs (shown in phantom at 350) to prevent closure of the auxiliary lumen 336. The inner wall 324 is made from the same types of flexible materials as described previously for the inner tubes used in the multiple auxiliary lumen embodiments. This particular embodiment is well-suited for use in those situations where a relatively large device lumen is required in favor of the advantages provided by multiple auxiliary lumens.

The outer wall 12 is preferably made from any of the well-known polymer materials used in fabricating introducers and other access devices. Exemplary materials include polyurethane, polyethylene, polypropylene, nylon, polyester, polyether/ester copolymers, silicone based polymers, metalocene catalyzed polyolefins or ethylene vinyl acetate and synthetic rubbers. Preferably, the material used and wall thicknesses for the outer wall 12 are such that the outer wall 12 is a relatively stiff tube in relation to the inner tube 24. Further, the material used for the outer wall 12 should be compatible for molding purposes with the material used to form the inner wall 24. It is preferred that the outer wall 12 and inner wall 24 be extruded together, as will be more fully described below. The outer wall 12 and inner wall 26 may be made from the same material or different materials. The inner wall 26 is preferably made from softer versions of the various polymers listed above. When using different materials, the materials must be compatible for bonding or fusing together.

Other fabrication techniques for connecting the inner and outer tubes are possible provided that the connection between the two lumens at the separation barriers 44 and 46 extends the entire length of the two lumens and provides a solid integral connection between the lumens. For example, radio frequency (RF) welding of the tubes is another possible fabrication procedure which may be used to make the access lumen in accordance with the present invention. If desired, the entire triple lumen can be extruded as a single integral multiple lumen structure.

During use, the exemplary access device 10 allows introduction of medical implements into the device lumen while at the same time allowing infusion of fluid through tube 66 also into device lumen, as well as allowing infusion through tubes 58 and 60 into auxiliary lumens 48 and 36, respectively. Since, as discussed above, the outer tube 12 is relatively inflexible in the radial direction (though overall longitudinally flexible), the total available cross-sectional area for insertion of medical implements and flow of fluids is limited for a given access device. However, the flexibility of the device lumen allows the doctor or other medical professional to selectively and fully utilize the total available cross-sectional area.

In FIG. 3A, a relatively small catheter 32 is shown inserted within the device lumen 30. In this configuration, fluids may be infused removed through the unused area of the device lumen 30 as well as the two auxiliary lumens 36 and 48. It should be noted that the preferred design inherently centers the catheter or medical implement 32 so that the auxiliary lumens 36 and 48 have approximately equal cross-sectional areas. However, it should be noted that the application of differential pressure to the infusion tubes 58 and 60 can be used to selectively increase or decrease the relative cross sectional areas available for infusion of fluids through the auxiliary lumens. For example, the size of auxiliary lumen 36 can be increased relative to the cross-sectional size of auxiliary lumen 48 by introducing the infusion of liquid through tube 58 at a pressure which is relatively higher than that of tube 60. The double auxiliary lumen design of this exemplary embodiment is especially well suited for providing such differential fluid flows when desired.

Figure 11A:
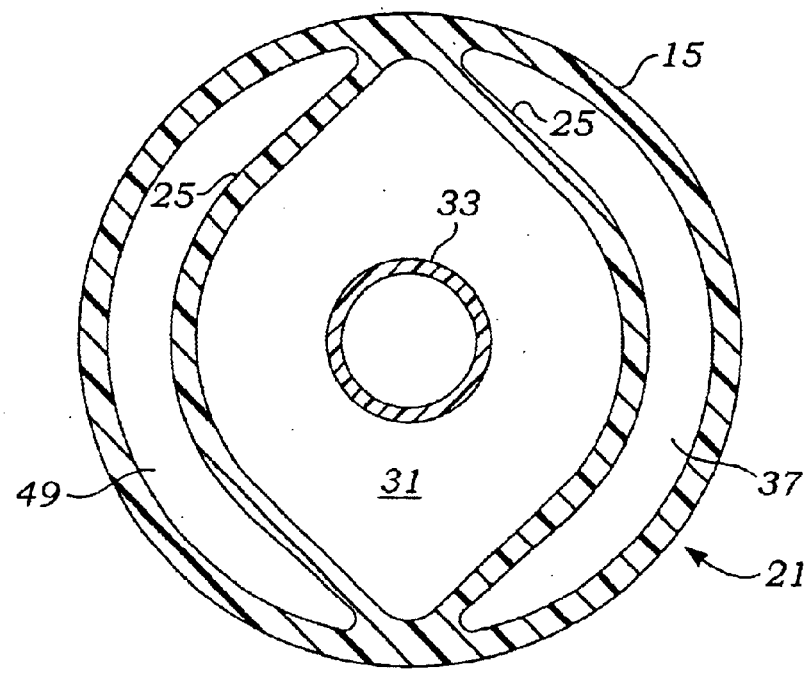
FIGS. 11A–C are sectional views of an exemplary multiple lumen access device showing a relatively small diameter medical implement located in a central device lumen and the inner walls in relaxed conditions (11A), partially collapsed about the implement due to pressurization of side auxiliary lumens (11B), and substantially completely collapsed about the implement (11C).
Figure 11B:
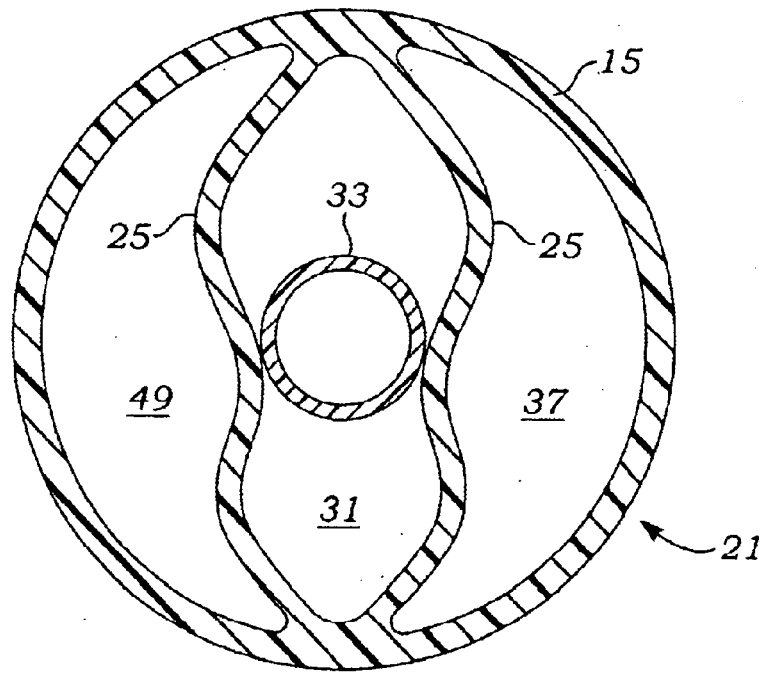
Figure 11C:
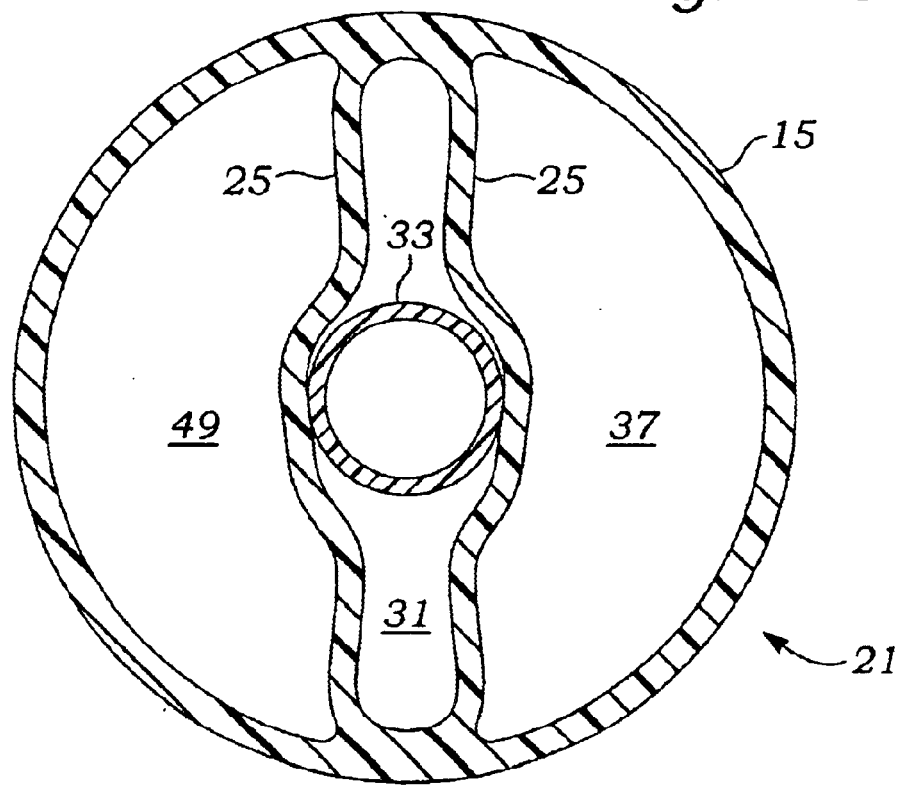

An exemplary embodiment which further demonstrates the flexibility of devices in accordance with the present invention is demonstrated in FIGS. 11A–11C. In FIG. 11A, an exemplary access device 21 is shown in which a relatively small catheter 33 is located within the device lumen 31. In this configuration, fluids may be infused/removed through the unused area of device lumen 31 as well as the two auxiliary lumens 37 and 49. As shown in FIG. 11A, the inner flexible walls 25 is in a relaxed position. In this position, the inner wall 25 is relatively close to the outer wall 15. When desired, the size of the auxiliary lumens 37 and 49 can be increased substantially by increasing the pressure of liquids being passed therethrough. The result, as shown in FIG. 11B, is the partial collapsing of the inner tube or inner walls 25 about the catheter 33. In the partially contracted or collapsed position as shown in FIG. 11B, the inner walls 25 are not stretched. Instead, their configuration changes as shown in FIG. 11B to accommodate the change in relative sizes of the auxiliary lumens and device lumen. As shown in FIG. 11C, the size of auxiliary lumens 37 and 49 are increased even further to a point where the fluid flow through the two auxiliary lumens is maximized. In this condition, stretching of the contracted flexible walls 25 may occur. As is apparent from FIGS. 11A–11C, it is possible to provide a wide variance in fluid flows through the auxiliary lumens and device lumen depending upon differential pressures applied through the various lumens.

Alternative Sheath Cross-Sections

Figure 13:
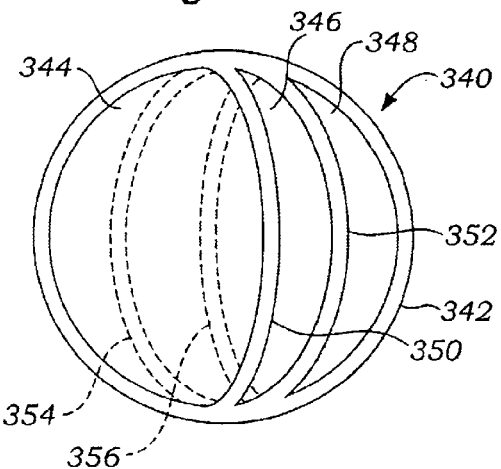
FIG. 13 is a sectional view of an alternative multi-lumen sheath for use in the present invention having a device lumen on one side and two side-by-side auxiliary lumens.

FIG. 13 illustrates an alternative cross-section of a sheath portion 340 for the multiple lumen access device of the present invention in which the device lumen is not between two auxiliary lumens. The sheath portion of the devices of the present invention comprise the portion that is distally disposed with respect to the junction housing, defines multiple lumens therein, and is substantially inserted into the patient's vasculature. In FIG. 13, the sheath portion 340 comprises an outer tube 342 defining within, and, in series from left to right, a device lumen 344, a first auxiliary lumen 346, and a second auxiliary lumen 348. A first flexible wall 350 separates the device lumen 344 from the first auxiliary lumen 346, while a second wall 352, that can be flexible or relatively rigid, separates the first and second auxiliary lumens 346, 348. The first flexible wall 350 can move from its position shown in solid line to the dashed-line position shown at 354 as the pressure difference across the wall increases in favor of the first auxiliary lumen 346. Likewise, the second flexible wall 352, if flexible, can move from its position shown in solid line to the dashed-line position shown at 356 as the pressure difference across the wall increases in favor of the second auxiliary lumen 348.

Figure 14:
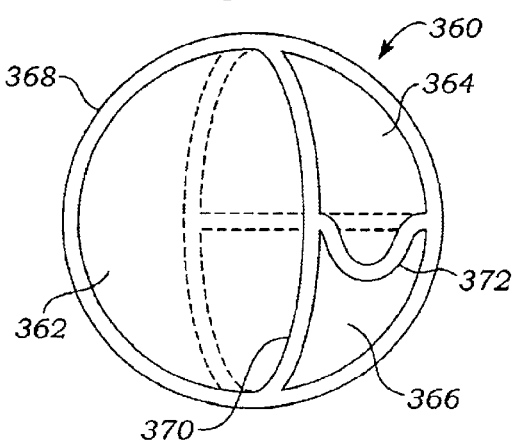
FIG. 14 is a sectional view of an alternative multi-lumen sheath for use in the present invention having a device lumen on one side and two stacked auxiliary lumens.

FIG. 14 is a further alternative cross-section of a sheath portion 360 for the multiple lumen access device of the present invention. The embodiment of FIG. 14 is similar to that shown in FIG. 13, and includes a device lumen 362, first auxiliary lumen 364, and second auxiliary lumen 366, all defined with an outer tube 368. In contrast to the embodiment of FIG. 13, the auxiliary lumens 364 and 366 are not arranged side-by-side, but are instead stacked on top of one another (at least in the orientation shown) so that both are located adjacent the device lumen 362. In this respect, a generally T-shaped internal dividing wall is provided including an elongated wall portion 370 and a shorter wall portion 372. The shorter wall portion 372 separates the first and second auxiliary lumens 364,366, while the elongated wall portion 370 separates the two auxiliary lumens from the device lumen 362. Both the elongated wall portion 370 and the shorter wall portion 372 are curvilinear in their relaxed configurations, shown in solid line in FIG. 14. The wall portions 370 and 372 straighten out into the dashed-line positions upon an increase in pressure in one or both of the auxiliary lumens 364, 366 relative to the device lumen 362.

In another alternative embodiment, not illustrated, the device lumen can be provided between two or more auxiliary lumens of different sizes. The device lumen is typically positioned off-center between crescent-shaped auxiliary lumens, and at least one of the auxiliary lumens can be expandable in accordance with the preceding discussion (that is, a wall between one of the auxiliary lumens and the device lumen is flexible). Desirably, there are two auxiliary lumens and the larger of the two lumens is expandable to enable infusion of large flow rates. In one particularly preferred embodiment, the larger lumen has a capacity equivalent to a gravity flow through a 14 gauge lumen.

Figure 15:
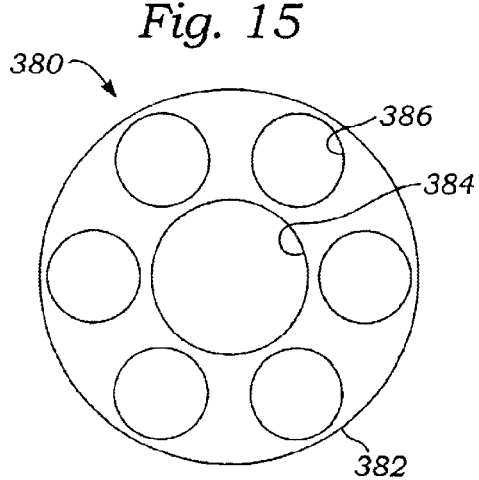
FIG. 15 is a sectional view of an alternative multi-lumen sheath for use in the present invention having no flexible walls therein.

FIG. 15 illustrates a still further cross-sectional view of a sheath portion 380 which may be used in conjunction with the multiple lumen access device of the present invention. In this embodiment, the sheath portion 380 includes a generally cylindrical solid member 382 having a central device lumen 384 and a plurality of auxiliary lumens 386 surrounding the device lumen formed therein. There are no flexible walls in this embodiment, it being understood that various aspects of the present invention may be advantageously utilized without the need for varying the cross-sectional shape of any of the lumens within the sheath portion 380. Alternatively, if desired, any wall portion separating the device lumen 384 from any of the auxiliary lumens 386 may be formed to be flexible to enable variability of the cross-section of that lumen.

Figure 12:
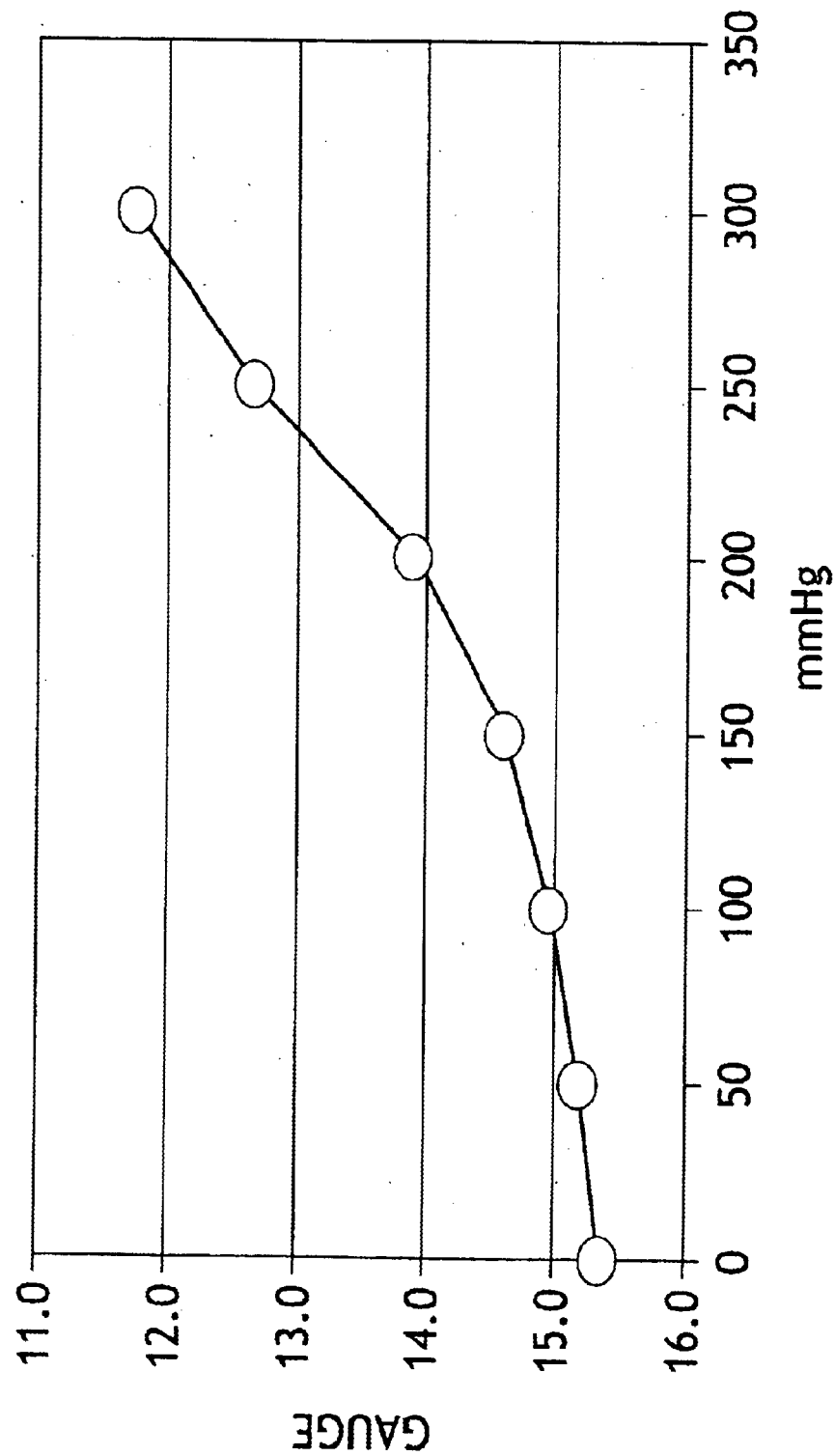
FIG. 12 is a graph illustrating an increase in the cross-sectional area (in gauge size) of an auxiliary lumen, such as in the cross-section shown in FIGS. 11A–11C, as the differential pressure between the auxiliary lumen and the device lumen changes.

The graph illustrated in FIG. 12 shows that as pressure inside the auxiliary lumen increases the cross-sectional area of that lumen increases. (The convention is that cross-section in terms of "gauge" numbers actually decreases for larger areas). FIG. 12 reflects the pressure response of one exemplary mutli-lumen catheter wherein the auxiliary lumen increases in size from about 15 gauge when there is no flow therethrough, to about 12 gauge with fluid infusion at a pressure of about 300 mmHg (in this sense, the 300 mmHg is the differential pressure across the flexible wall, if the assumption is made that the device lumen is at atmospheric pressure). The response curve of the increase in lumen size indicates that the flexible wall is sufficiently rigid to withstand small changes in pressure. From 0–150 mmHg, the auxiliary lumen increases only from slightly smaller than 15 gauge to slightly larger than 15 gauge. Only above 150 mmHg pressure differential does the lumen size significantly increase. This response is a factor of the thickness, shape and material of the flexible wall between the device and auxiliary lumens.

One of the advantages of having an inner wall 25 (as seen in FIG. 11A) or inner wall 350 (as seen in FIG. 13) which is flexible but also sufficiently rigid is that a pressure transducer may be connected to the multi lumen access device of the present invention to monitor a central venous pressure of a patient. In particular, the pressure transducer (not shown) may be placed in communication with one of the auxiliary lumens 37 and 49 to measure the central venous pressure. Advantageously, the resistance to small pressure differentials described above enables more accurate pressure monitoring, because the flexible wall does not substantially flex upon small differentials in pressure, and thus does not dampen or attenuate the resultant pressure wave sensed externally to the lumen. Specifically, the flexible inner walls 25 have sufficient stiffness to avoid significant damping or attenuation of pressure pulses in the auxiliary lumens 37 and 49, and do not undergo major flexing from small pressure differentials as shown in FIG. 12.

Figure 11D:
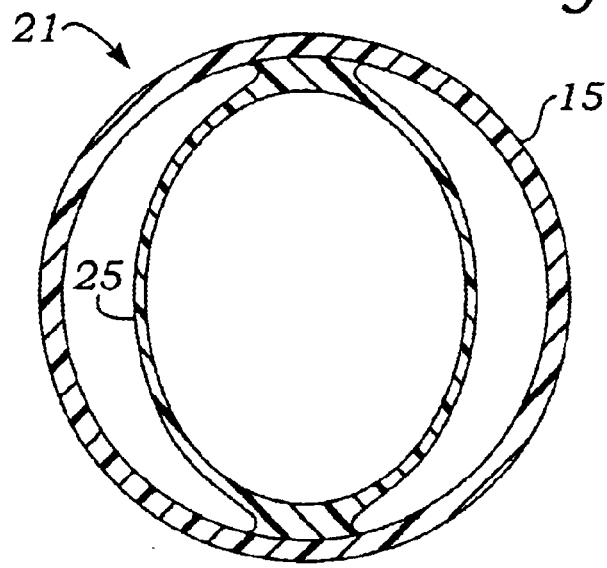
FIG. 11D is a sectional view of an alternative multiple lumen access device having flexible walls made of a material different from the material of the outer tube of the multiple lumen access device.

As described previously in regards to the exemplary embodiment illustrated in FIGS. 1–5, the outer wall 15 of the embodiment illustrated in FIGS. 11A–11C is preferably made from any of the well-known polymer materials used in fabricating introducers and other access devices. Preferably, the material used and wall thickness for the outer wall 15 are such that the outer wall 15 is a relatively stiff tube in relation to the inner walls 25 in the radial direction. Further, the material used for the outer wall 15 should be compatible for molding purposes with the material used to form the inner walls 25. It is preferred that the entire cross-section of the multi-lumen portion of the device 10, including the outer tube 12 and inner walls 25, is extruded together from a homogeneous material. Alternatively, the outer wall 15 and inner walls 25 may be coextruded and the junctions 27 be formed molding of the inner 25 and outer wall 15 together during the coextrusion process, as seen in FIG. 11D. Therefore, outer wall 15 and inner walls 25 may be made from the same material or different materials, as shown in FIG. 11D. The inner wall 25 is preferably made from softer versions of the various polymers listed previously. When using different materials, the materials should be compatible for bonding or fusing together.

The above described exemplary embodiments may be used in the same manner as conventional introducer devices. Additionally, if desired, the devices may be used in the same manner as conventional central venous pressure catheters. As will be appreciated by those skilled in the art, the present invention provides the design flexibility to allow use as a single device where the capabilities of an introducer device and catheter are simultaneously required. For example, many diagnostic and invasive medical procedures require the insertion of guide wires and/or medical devices, while simultaneously monitoring critical bodily functions and introducing or removing fluids as needed. The access device of the present invention allows all of the above functions to be performed simultaneously and selectively through a single access device.

MLADJ with Valve Insert

Figure 16:
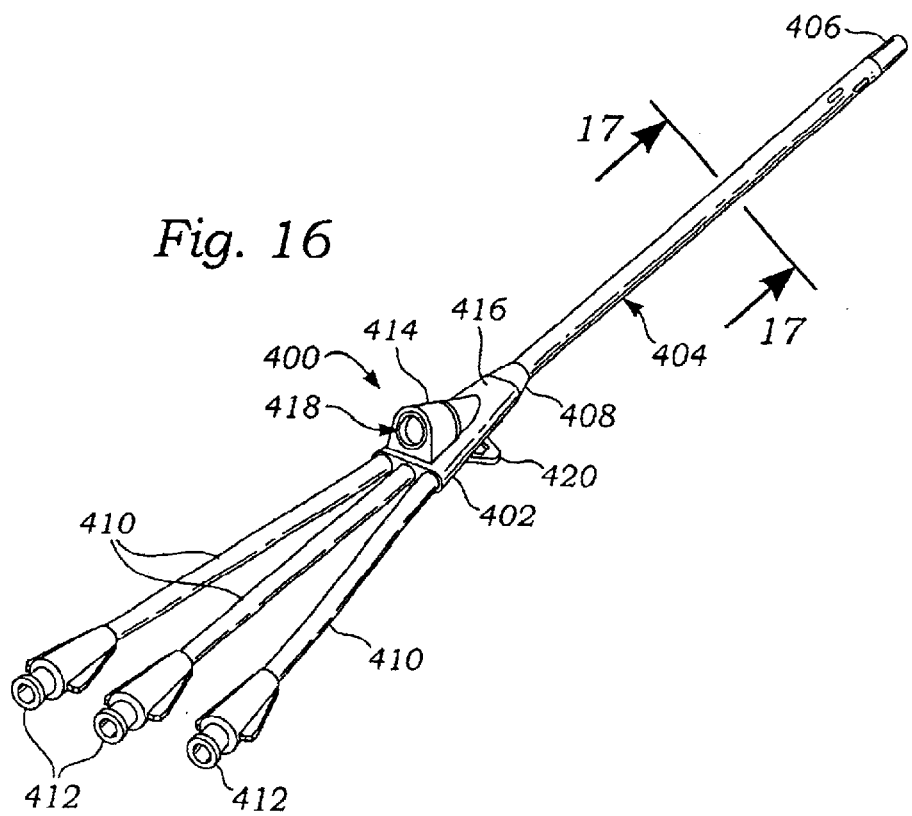
FIG. 16 is a perspective view of a further embodiment of a multiple lumen access device in accordance with the present invention.

FIG. 16 illustrates an alternative multiple lumen device 400 (MLAD) in accordance with the present invention with an improved junction housing 402. The device 400 is similar to the FIGS. 1–5, and includes a multiple lumen sheath 404 extending distally from the housing 402. The multiple lumen sheath has a distal end 406 for insertion in a body cavity and a proximal end 408 attached to the housing 402. A plurality of extension tubes 410 is attached to the proximal end of the housing 402 and terminate in luer connectors 412. The housing comprises a valve insert portion 414 and a low profile lumen portion 416. A valve insert 418 is secured in a cavity defined in the portion 414. A pair of mounting wings 420 is integrally formed with the junction housing 402 for attaching to a patient.

Figure 17:
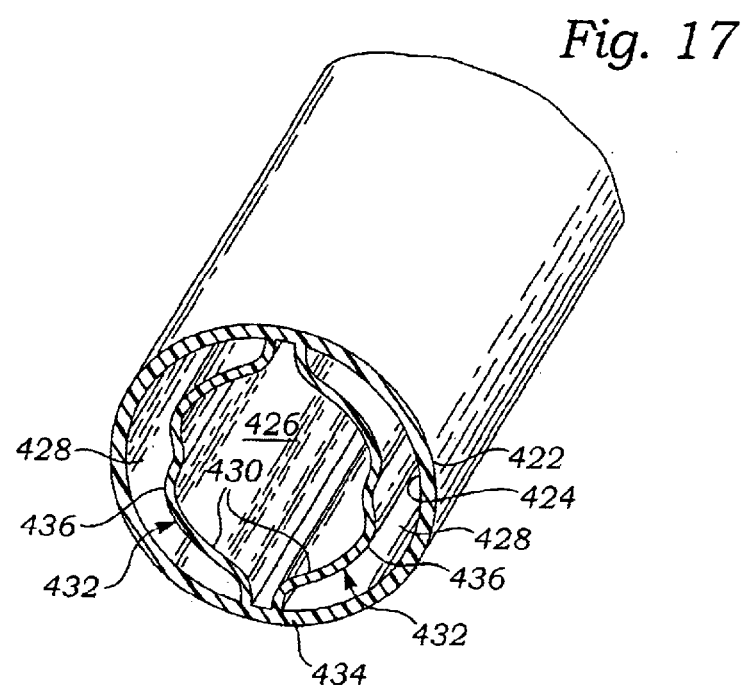
FIG. 17 is a perspective sectional view of FIG. 16 taken in the 17—17 plane.

The multiple lumen sheath 404 seen in cross-section in FIG. 17 comprises an outer circular tube 422 having an interior surface 424. In the illustrated embodiment, the multiple lumen sheath 404 includes a central device lumen 426 and a pair of auxiliary lumens 428 disposed on opposite sides of the device lumen. The device lumen 426 is defined between interior surfaces 430 of a pair of divider walls 432. The divider walls extend in a non-linear fashion substantially across the entire outer tube 422 and terminate at junctions 434. The junctions 434 are spaced a slight distance from one another so that the sheath 404 does not exhibit the separation barriers, as previously described. As illustrated, the device lumen 426 is generally concentrically positioned within the outer tube 422 and has a nominal diameter of slightly greater than half the outer tube 422. Between exterior surfaces 436 of the divider walls 432 and the interior surfaces 424 of the outer tube 422, the auxiliary lumens 428 are formed. The lumens 428 are substantially crescent shaped and are shown identical in size. Of course, as described previously, various other lumen configurations can be provided in the multiple lumen sheath 404.

Figure 19:
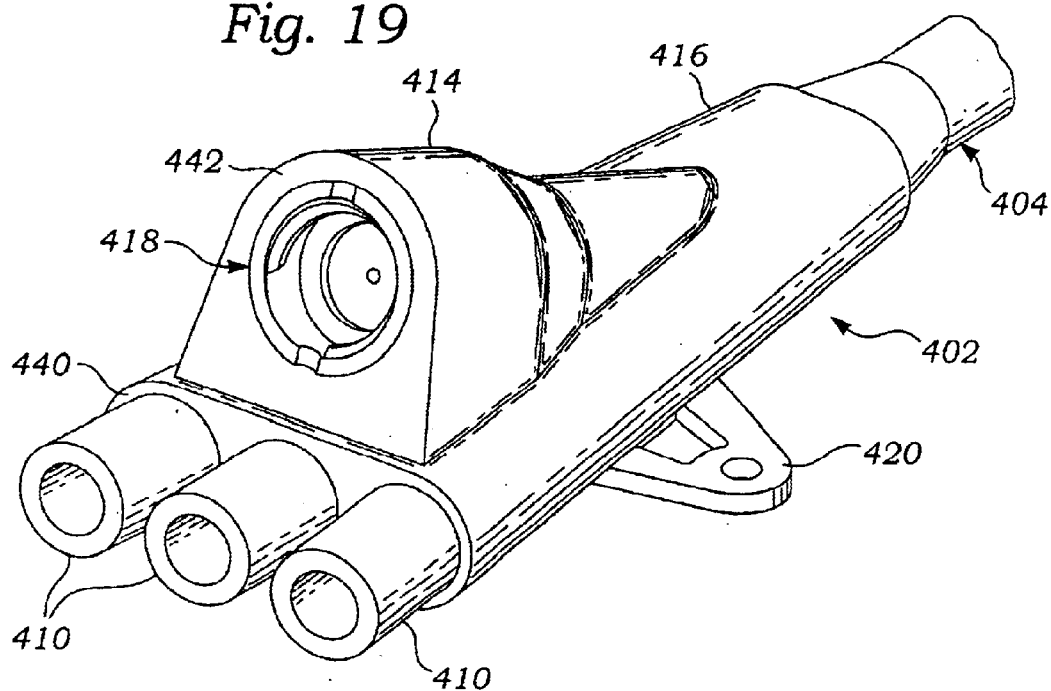
FIG. 19 is an enlarged perspective view of a junction housing of the device shown in FIG. 16.
Figure 20:
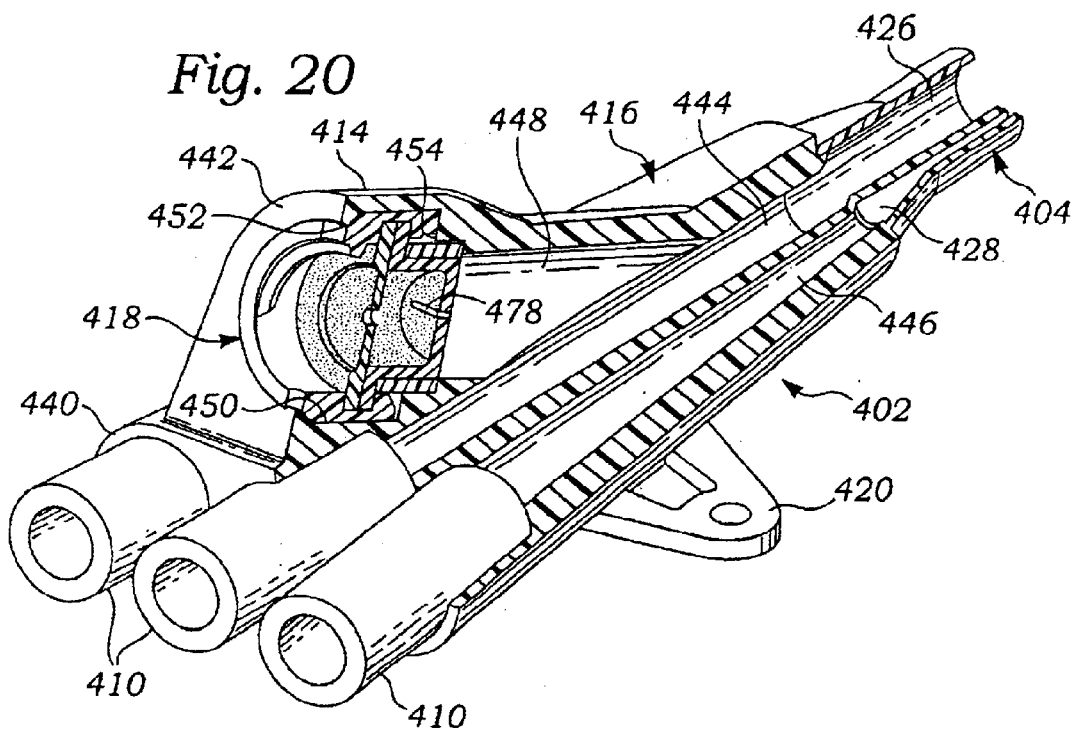
FIG. 20 is an enlarged perspective of the junction housing of FIG. 19 with a portion cut away on the longitudinal axis.

The junction housing 402 is illustrated in greater detail in FIGS. 19 and 20. The low profile lumen portion 416 has an oval cross-section tapering gradually wider along its long axis from the multiple lumen sheath 404 to a proximal face 440 to which the extension tubes 410 connect. The valve housing portion 414 angles upward from one wide surface of the lumen portion 416 and terminates in a proximal face 442. The device access valve insert 418 fits within an angled cavity formed in the valve housing portion 414. With specific reference to FIG. 19, the lumen portion 416 comprises a main channel 444 and a pair of auxiliary channels 446 on either side. The main channel communicates with a central extension tube 410, while the auxiliary channels 446 communicate with the side extension tubes. A device channel 448 defined within the valve housing portion 414 is in communication with the main channel 444 and angles upwardly therefrom to terminate in a widened cavity 450. The cavity 450 receives the valve insert 418 which is held therein by a circumferential lip 452 on the outermost portion of the cavity 450. The cavity 450 continues inward from the lip 452 towards the device channel 448 and narrows at a step 454. The step 454 provides a stop surface against which the valve insert 418 is pressed. Desirably, the insert 418 and cavity 450 are keyed to facilitate insertion in a particular rotational orientation and prevent further rotation.

Valve Insert

Now with reference to FIGS. 21 and 22, the device access valve insert 418 is seen in greater detail. The valve insert 418 comprises four components: an outer frame 460, a wiper 462, a valve 464, and a sleeve 466. The assembled valve insert 418 is seen in FIG. 18. The wiper 462 and valve 464 are juxtaposed within an outer wall 468 of the frame 460, and held therein by the interaction between a flange 470 of the sleeve 466 and a pair of cantilevered latches 472 provided on the frame. The sleeve 466 further includes a support tube 474 projecting downward from the flange 470 and surrounding the valve 464. The wiper 462 includes an aperture 476 through which device catheters may be inserted in a sealed fashion. The valve 464 may be a conventional duck-billed valve having a valve slit 478, as seen in FIG. 17. The combination of the wiper 462 and the valve 464 effectively seals the device channel 448 formed within the junction housing 402 and the exterior of the junction housing when devices are repeatedly introduced and withdrawn through the valve insert 418. The outer wall 468 further includes a pair of partial threads 480 which cooperate with exterior threads on an infusion catheter dilator or contamination shield (not shown).

The entire valve insert 418 is formed separately from the junction housing 402, which is molded from a soft, flexible material, typically a soft thermoplastic material. The softness of the junction housing 402 is important in enhancing patient comfort and flexibility of the entire multi-lumen access device 400 when assembling and mounting to a patient. Conversely, the fame 460 of the valve insert 418 is relatively rigid for supporting the wiper 462 and duck-billed valve 464. The wiper and duck-billed valve are made of elastomeric materials, and the outer wall 468 prevents valve depression or distortion and thus enhances the patency of the seal formed by the valve insert 418. The sleeve 466 stabilizes the elastomeric valve components, and the support tube 474 provides an outer surface against which the duck-billed valve 464 cannot extend past. The rigidity of the valve insert 418 provides structure to facilitate connection of devices thereto. Furthermore, the junction housing 402 is easily injection molded over the multiple lumen sheath 404 and tubes 410 prior to addition of the insert 418, for a simplified manufacturing process.

Sheath Cross-section Formation and Details

Figure 18A:
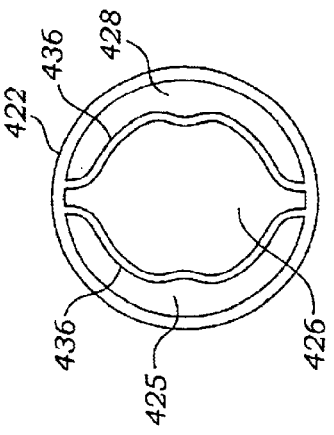
FIG. 18A is a perspective view of an extrusion die for making a sheath portion of the multiple lumen access device of the present invention.

FIG. 18A illustrates in perspective an extrusion die 390 used to extrude a preferred cross-section of sheath portion of a multiple lumen access device of the present invention, such as the cross-section shown in FIG. 17. The extrusion die 390 comprises a large tubular member 392 having a bore 393, and a plurality of lumen-forming mandrels positioned longitudinally therein. Specifically, a device lumen-forming mandrel 394 and two surrounding auxiliary lumen-forming mandrels 396a, 396b are positioned within the bore 393 using elongated pins (not shown) closely fitting within guide holes 398.

Figure 18C:
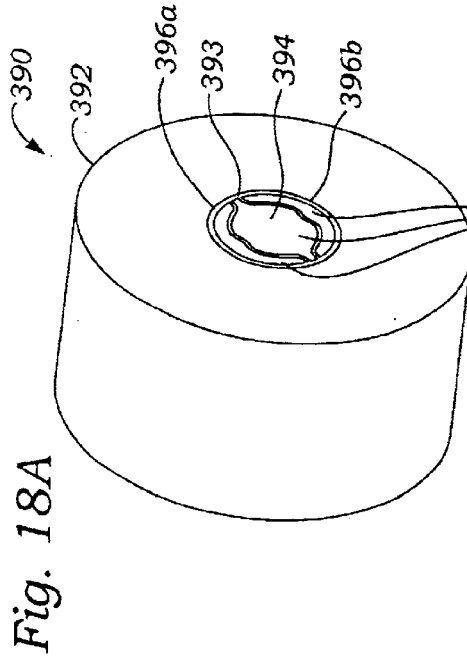
FIGS. 18C and 18D are isolated views of inner extrusion molds of the die shown in FIG. 18A with exemplary dimensions for the sheath portion cross-section called out.
Figure 18B:
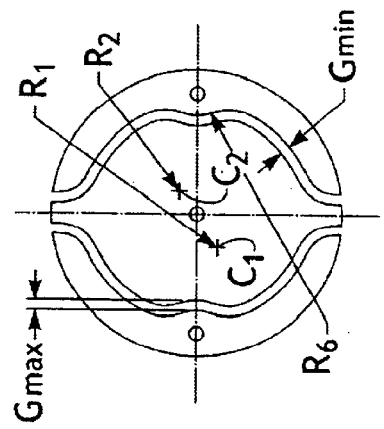
FIG. 18B is an end view of a sheath portion of the multiple lumen access device as extruded from the die shown in FIG. 18A.

As it is known in the extrusion art, material such as polyurethane in liquid form can be forced through the cavities formed between the bore 393 and the mandrels 394, 396 and gradually cooled so that when the material exits from the extrusion cavity it has solidified somewhat and retains the shape shown in FIG. 18B.

FIG. 18B is a cross-sectional view of the exemplary sheath 404 of FIG. 16 and includes an outer tube 422 and two inner walls 436 together defining device lumen 426 and the surrounding auxiliary lumens 428, as described in more detail below.

Figure 18D:
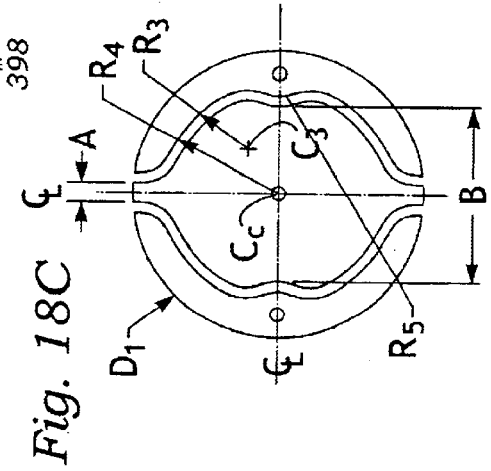

FIGS. 18C and 18D are more detailed views of the surfaces of the mandrels 394 and 396 in one preferred embodiment of the present invention. The outer diameter of the auxiliary lumen-forming mandrels 396 is given as $D_1$, and the outer surfaces are centered about axis $C_0$. The inner surfaces of the mandrels 396 are defined by several arcs. As seen in FIG. 18D, a first inner surface portion as a radius $R_1$ centered about axis $C_1$, while second portion has radius $R_2$ centered about axis $C_2$.

The device lumen-forming mandrel 394 includes two diametrically opposed ribs 398 having a thickness A, and a central non-uniform convex body defined by several arcs that generally conform to the inner surfaces of the auxiliary lumen-forming mandrels 396. More specifically, the exemplary mandrel 394 includes convex surfaces that are identical in the four quadrants shown and have a first radius $R_3$ centered about axis $C_3$, and a second radius $R_4$ centered about axis $C_0$. A minimum gap indicated at $G_{min}$ is defined between the convex outer surfaces of the device lumen-forming mandrel 394, and the concave inner surfaces of the auxiliary lumen-forming mandrels 396. The minimum gap $G_{min}$ thus forms the thinnest portions of the walls 436 of the device of the present invention.

Along the diametric plane that is normal to the diametric plane through the ribs 398, both extrusion mandrels exhibit a curvature toward the axis $C_0$. Namely, the device lumen-forming mandrel 394 has a concave outer surface portions with the radius $R_5$, and both of the auxiliary lumen-forming mandrels 396 have a convex portion with a radius $R_6$. The configuration of these curvilinear portions creates a maximum gap between the mandrels indicated at $G_{max}$. The maximum gap $G_{max}$ thus forms the thickest portions of the walls 436. The walls 436 are initially spaced apart a distance B.

Exemplary dimensions of the extrusion die and the corresponding cross-section of the device sheath are given in the table below:

TABLE I

| Extrusion Mandrel Configuration | |
| --- | --- |
| DIMENSION | VALUE (in, mm) |
| $D_1$ | 0.325, 8.26 |
| $R_1$ | 0.172, 4.37 |
| $R_2$ | 0.0956, 2.43 |
| $R_3$ | 0.0574, 1.46 |
| $R_4$ | 0.1195, 3.04 |
| $R_5$ | 0.0382, 0.97 |
| $R_6$ | 0.0201, 0.51 |
| A | 0.0306, 0.78 |
| B | 0.2007, 5.10 |
| $G_{min}$ | 0.0099, 0.25 |
| $G_{max}$ | 0.0182, 0.46 |

The dimensions shown in Table 1 are strictly exemplary, and the multiple-lumen access device of the present invention by no means is limited to these particular dimensions.

The resultant cross-section of the sheath after extrusion through the die 390 is seen in both FIGS. 17 and 18B. The two walls 436 each connect to the outer tube 422 at closely-spaced locations that are approximately diametrically opposed. The walls 436 bow away from one another in their relaxed states, with each generally following the curvature of the outer tube 422 to form therebetween the auxiliary lumens 428. The device lumen 426 is formed between the walls 436 which are well-suited to collapsing upon a positive pressure gradient generated between an auxiliary lumen 428 and the device lumen. That is, the narrow gaps $G_{min}$ formed in the extrusion die create regions in each wall 436 that are weak in bending. As the pressure differential across the walls 436 increases in favor of the auxiliary lumen 428, the thickest portion created by the gap $G_{max}$ tends to be forced inward first because of the bending of the thinnest portions. If a device is positioned within the device lumen 426, the walls 436 will contact it at the thickest portions first. This behavior is shown for a different sheath cross-section in FIGS. 11A–11C. As a result, the line contact between the walls 436 and the device facilitates sliding movement of the device through the sheath. That is, the walls 436 bend such that a large surface area is prevented from contacting the device, and thus the frictional resistance to sliding movement is minimized.

Alternative MLAD with Valve Insert

Figure 23B:
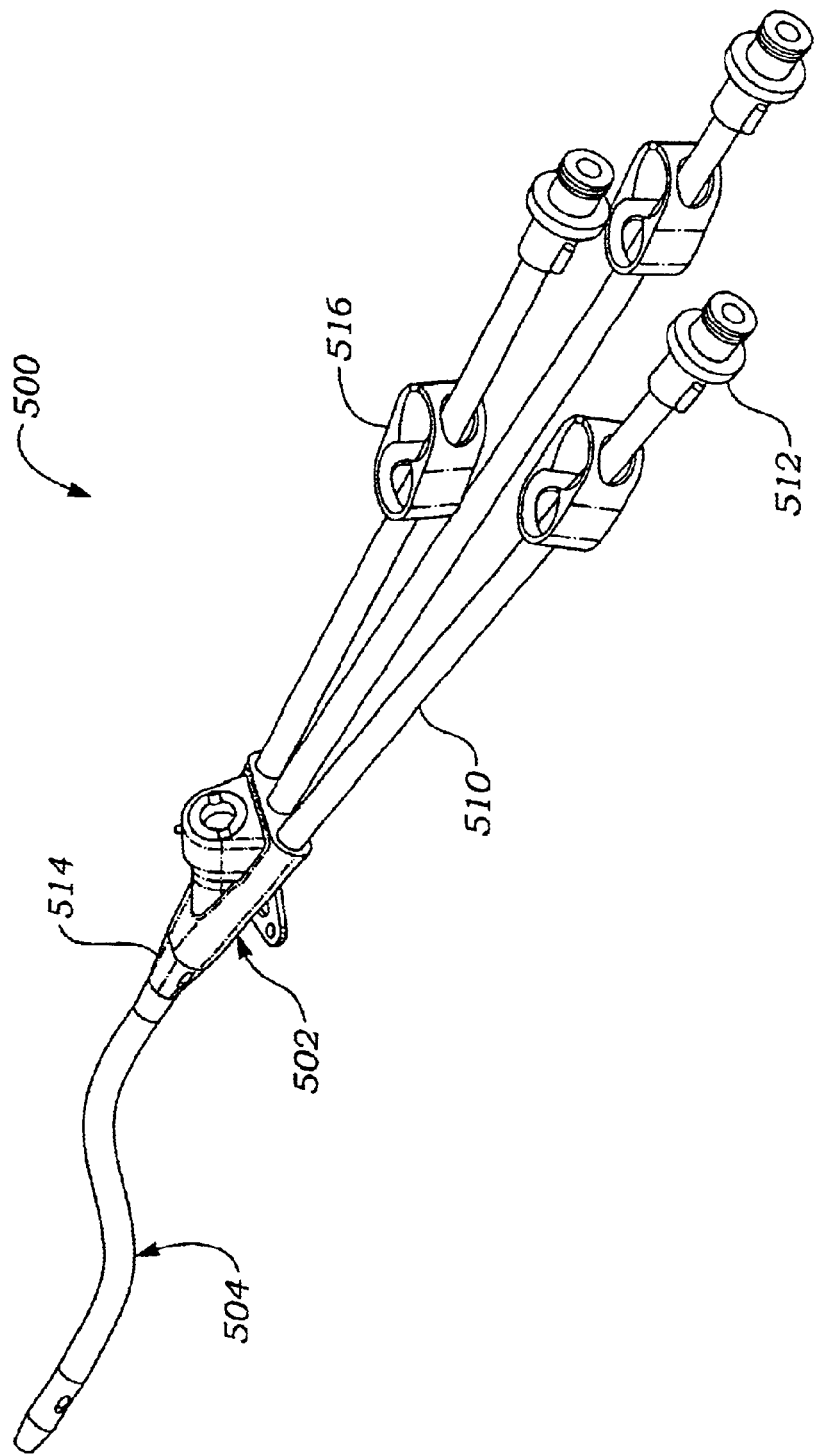

FIGS. 23A and 23B are different perspective angles of an exemplary multiple lumen access device 500 of the present invention, which is in many respects very similar to the device 400 shown in FIG. 16. The device 500 includes a junction housing 502, a distal sheath 504, and a plurality of proximal extension tubes 510 terminating in luer connectors 512. One of the main distinctions from the earlier described embodiment is the provision of a strain relief insert 514 positioned at the distal end of the junction housing 502. In addition, an alternative device valve insert is provided, but is not seen in FIGS. 23A and 23B and will be described in detail below. Finally, a plurality of conventional finger-actuated clamps 516 are mounted on the extension tubes 510.

FIG. 24 is a side elevational view of the device 500 of FIG. 23 showing the distal sheath 504 inserted through the outer tissue 518 of a patient and into a vessel 520. The flexible nature of the sheath 504 is seen in this figure, as well as the ability of the junction housing 502 to live flat against the patient's skin. As mentioned above, the material used and wall thicknesses for the outer tube of the sheath 504 are such that the outer tube is a relatively stiff tube in relation to the inner flexible walls. Nevertheless, the entire sheath 504 is sufficiently pliable so as to enable slight bending along its length which facilitates insertion into the patient's vessel and comfortable placement against the skin. The soft material used in making the junction housing 502 further prevents irritation to the patient. In addition, the strain relief insert 514 is located adjacent the most extreme bend of the sheath portion 504 and helps prevent kinking of the internal lumens.

Alternative Valve Insert

Figure 27:
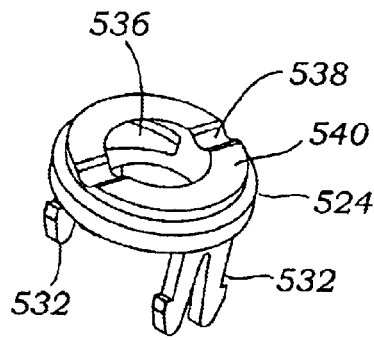
FIG. 27 is a perspective view of a clamp portion for the valve insert of FIG. 26.
Figure 26:
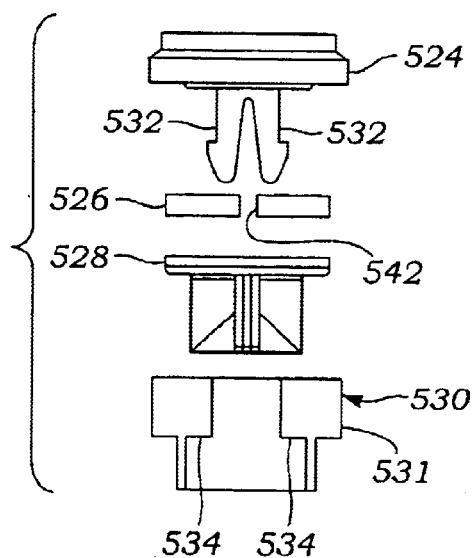
FIG. 26 is an exploded elevational view of the valve insert shown in FIG. 25A.
Figure 25B:
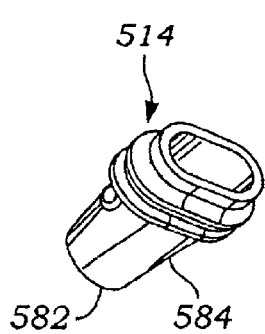
FIG. 25B is a reversed perspective view of the strain relief insert adapted to be coupled to the junction housing in FIG. 25A.
Figure 25A:
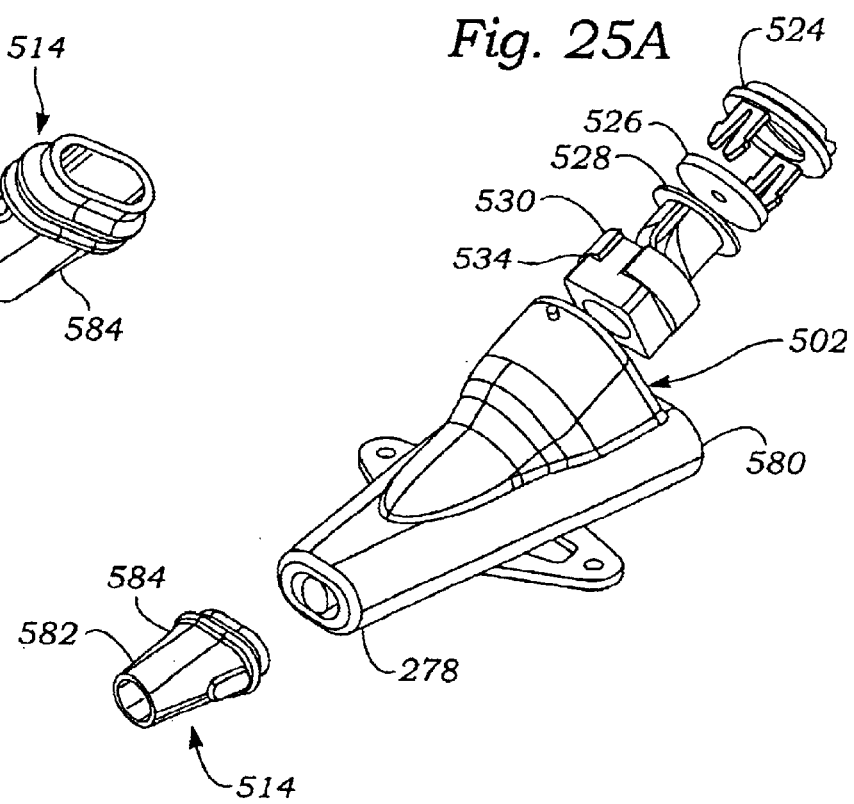
FIG. 25A is a perspective view of a junction housing of the device shown in FIGS. 23 and 24 showing a valve insert and strain relief insert both exploded therefrom.

FIG. 25A is a perspective view of the junction housing 502 with the strain release insert 514 exploded from the distal and, and components of an alternative device lumen valve insert 522 exploded from the proximal end. The strain relief insert 514 is additionally shown at a different angle in FIG. 25B. FIGS. 26 and 27 illustrate the components of the alternative valve insert 522 in greater detail.

FIGS. 26 and 27 illustrate the alternative device access valve insert 522 which includes a tactile feedback feature. The valve insert 522 comprises four components: a clamp 524, wiper 526, valve 528, and lower outer frame 530. The wiper 526 and valve 528 are juxtaposed within an outer wall 531 of the lower outer frame 530, and held therein by the securement of the clamp 524 onto the lower outer frame 530 by a pair of latches 532 which engage with mating lugs 534. The clamp 524 includes a pair of partial threads 536 which cooperate with exterior threads of an infusion catheter dilator or contamination shield (not shown). A pair of grooves 538 is disposed on a contact face 540 of clamp 524.

The wiper 526 includes an aperture 542 through which device catheters may be inserted in a sealed fashion. The valve 528 may be a conventional duck-billed valve having a valve slit, as seen at 464 in FIG. 22. As described previously in regards to the device valve insert 418 shown in FIGS. 21 and 22, the combination of the wiper 526 and the valve 528 effectively seals the device channel formed within the junction housing and the exterior of the junction housing when devices are repeatedly introduced and withdrawn through the valve insert 522.

The upper portion of the valve insert 522 is relatively rigid and may be formed from the same material as the lower outer frame 530 such as acrylic, polysulfone, or other high durometer materials. It is also noted that the valve insert 522 shown in FIG. 26 may be used for the exemplary multi-lumen access devices shown in FIGS. 1, 6 and 16.

Contamination Shield Adapter

Figure 28A:
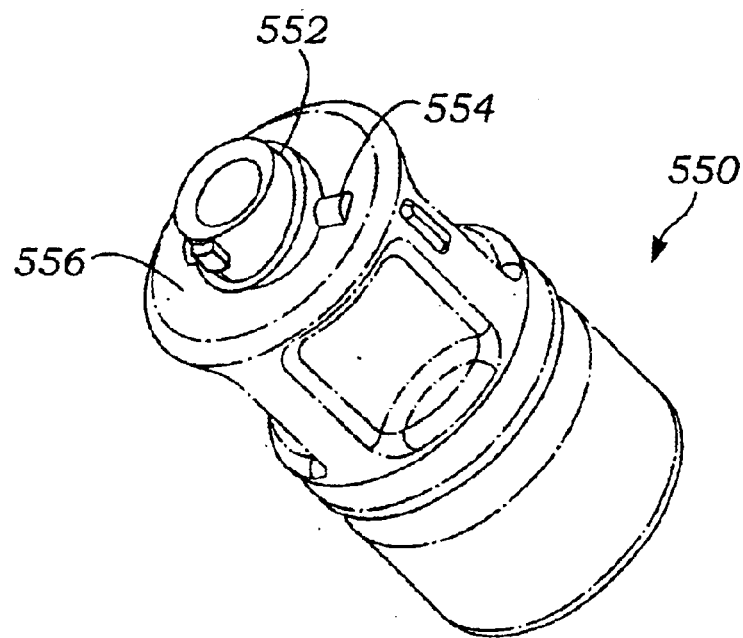
FIGS. 28A and 28B are perspective views of an adapter which mates with the valve inserts of FIGS. 21 or 26.
Figure 28B:
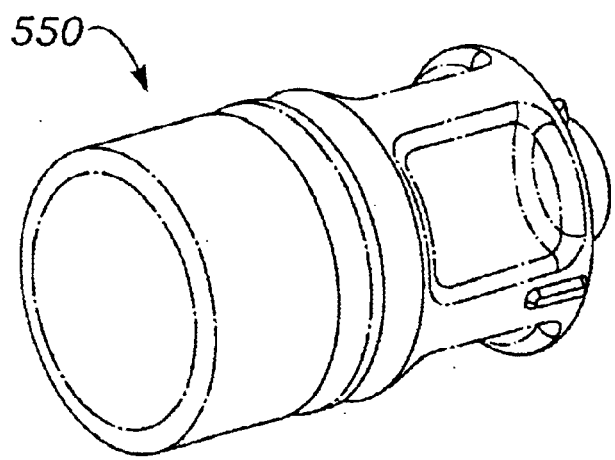

FIGS. 28A and 28B illustrate an adapter 550 for a distal end of a contamination shield. The adapter 550 includes threads 552 which mate with the threads 536 of the upper portion of the valve insert 532 illustrated in FIGS. 26 and 27. The threads 552 of the adapter 550 are designed to fully engage with the threads 536 of the clamp 524 by a ¼ turn of the adapter 550. A pair of lugs 554 are disposed on the contacting surface 556 of the adapter 550 such that the lugs 554 mate with the pair of grooves 538 of the clamp 524. As the ¼ turn is completed, the lugs 554 snap into the grooves 538 and create a tactile feedback. The contamination shield 550 sealingly receives a flexible tubular sheath thereover to provide a sterile channel that is alternately collapsible and extensible around devices inserted through the device valve. Such contamination shields are well known in the art and will not be further described.

Strain Relief Insert

A multiple lumen access device may kink at the multi-lumen sheath/junction housing interface when the access device is attached to a patient. The kink may reduce the cross-sectional area of the multi-lumen sheath or in extreme circumstances, result in blockage of the lumens. The "kink" problem may be resolved by providing a multiple lumen access device with the strain relief insert 514 as illustrated in FIGS. 23A, 23B, 24, and 25A. Again, the access device 500 is similar to the access device described in FIG. 16 with the exception that the junction housing 502 is modified to accept the strain relief insert 514. The strain relief insert 514 is connected to the distal end of the junction housing 502, and over the multi-lumen sheath 504.

The strain relief insert 514 has an oval cross-section tapering gradually wider along its long axis from the multi-lumen sheath 504 to the junction housing 502. As seen in FIG. 25A, the low profile lumen portion 578 of the junction housing 502 also has an oval cross-section tapering gradually wider along its long axis from the strain relief insert 514 to a proximal face 580 to which the extension tubes (not shown) connect. The strain relief insert 514 includes a tapered body 582 having ribs 584 which gradually blend into the body. These ribs 584 allow the strain relief insert 514 to flex and prevent the multiple-lumen sheath 504 from kinking.

In order to achieve the desired flexibility of the strain relief insert 514, it is preferred that a relatively soft, elastic material be utilized. Suitable elastic materials include, but are not limited to, polyurethane and pellathane with a 55D shore hardness. Further, in order to achieve the desired flexibility, the thickness of the strain relief insert 514 must be carefully matched to the particular material being utilized. For less flexible materials, the wall thickness should be correspondingly reduced in order to achieve the desired flexibility limits. The strain relief insert 514 may be formed using radio frequency (RF) technology with appropriate forming dies and fixtures. Desirably, the strain relief insert 514 is overmolded onto the sheath 504 and subsequently coupled to the junction housing 502 at the time that the housing and sheath are connected.

MLADS with Remote Introducer Valves

FIGS. 29 and 30 illustrate a further embodiment of the multiple lumen access device 600 in which the device access valve 602 is not formed integrally with the junction housing 604. More particularly, as best seen in FIG. 29, the junction housing 604 has a low profile which is slightly greater than the sheath 606 or extension tubes 608 attached thereto. FIG. 31 shows a proximal end of low profile junction housing 604 illustrating three channels 610 formed therein for communication with three extension tubes 612, seen in FIG. 30. A central extension tube 612 connects with a remote introducer valve 614 which has a proximal opening 616 for device catheter access. Within the introducer valve 614, a number of different duck-bill or other valves may be provided to seal the lumen of the extension tube 612 from the exterior. Introducer valve 614 may include a side port extension tube 618 terminating in a luer lumen hub 619 for attaching to infusion fluid sources. Thus, in this alternative configuration, a single needle stick followed by implantation of the multi-lumen sheath 606 is all that is required to obtain the benefits of both an introducer valve and central venous catheter, as described previously. Alternatively, the multiple lumen access device 600 further includes an auxiliary lumen valve connected to at least one other extension tube 612 than the central tube to therefore provide a valved entry to at least one of the auxiliary lumens within the sheath 606 as well as with the device lumen.

Figure 32:
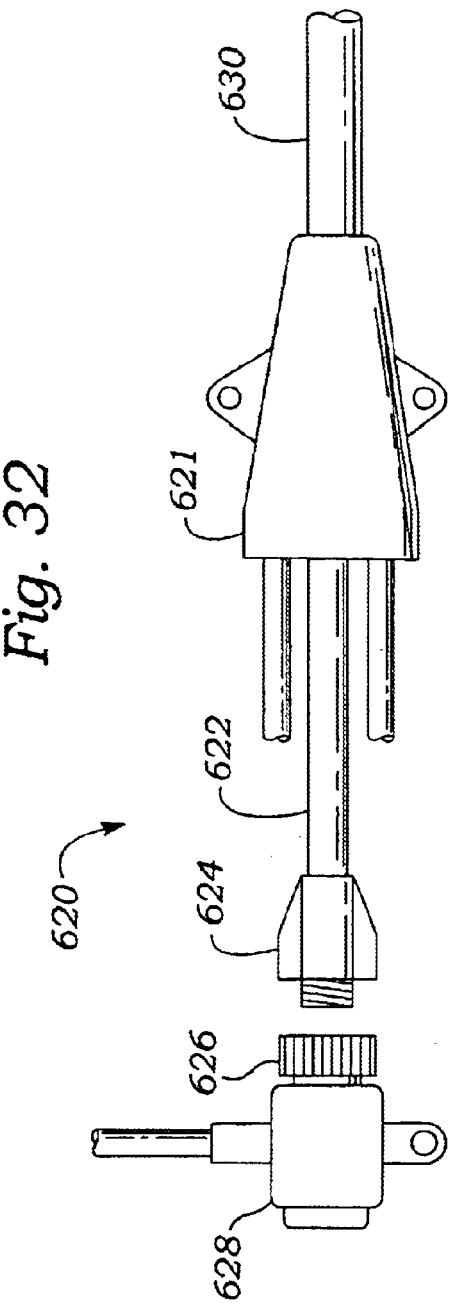
FIG. 32 is a plan view of an alternative multiple lumen access device with a low profile junction housing.
Figure 33:
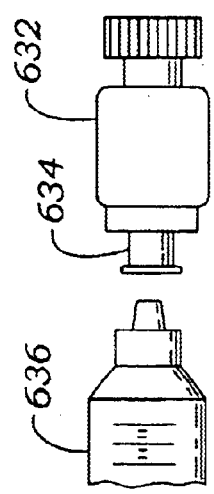
FIG. 33 is a detailed view of an alternative introducer valve assembly for use in the device of FIGS. 30 or 32.

In a further alternative of the device 600, FIG. 32 illustrates a multiple lumen access device 620 wherein the central extension tube 622 terminates in a luer connector 624. The luer connector 624 is desirably used to mate with a female luer connector 626 of an introducer valve assembly 628. However, in this detachable configuration, various other medical devices having conventional luer fittings may be attached to the luer connector 624 and placed in communication with a central lumen of the multi-lumen sheath 630. FIG. 33 illustrates a further alternative, wherein the introducer valve assembly 632 is provided with a male luer connector 634 on a proximal end to which an infusion syringe 636 may be attached. As can be seen, various configurations are possible with the remote introducer valve assembly 628, and the low profile junction housing 621 is easily molded over the extension tubes and has a reduced size, thus facilitating the manufacturing process.

MLAD with Multi-lumen Catheter and/or Introducer Combination

Figure 36:
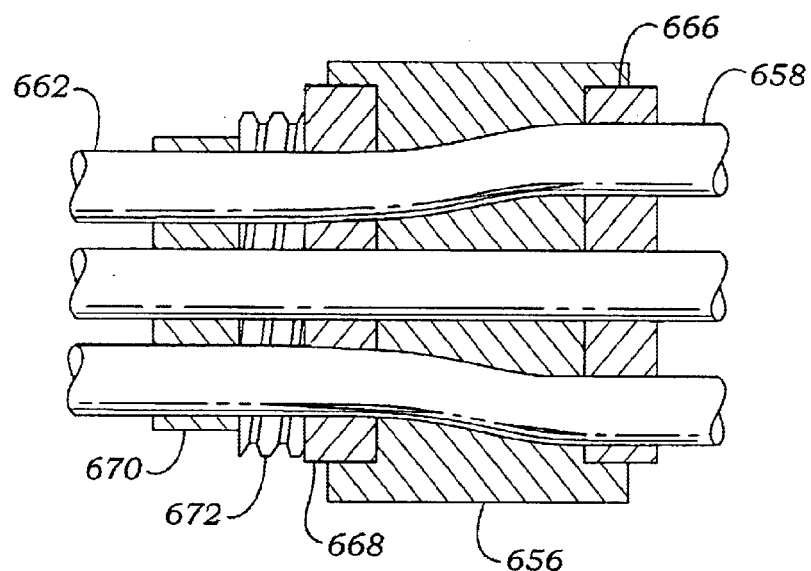
FIG. 36 is a sectional view of a junction housing used in the device of FIG. 34.

FIG. 34 illustrates a further alternative multiple lumen access device 650 comprising a multi-lumen infusion catheter 652 in combination with a conventional single-lumen introducer valve 654. The multi-lumen infusion catheter 652 includes a junction housing 656 which interfaces a plurality of proximal extension tubes 658 and a multi-lumen sheath 660 extending distally therefrom. FIG. 36 illustrates one way in which the proximal extension tubes 658 can be routed to communicate with a plurality of tubes 662 providing lumens of the multi-lumen sheath 660. The multi-lumen sheath 660 is sized to fit through the introducer valve 654 having a distal sheath 664, and from there into the body. In this manner, a single-lumen introducer may be implanted into the patient and then used further as an access port for the multi-lumen infusion catheter 652. By leaving the introducer in place, only a single stick is necessary to enjoy both introducer and central venous catheter capabilities.

With specific reference to FIG. 36, a proximal insert 666, and a distal insert 668 are mounted around the array of extension tubes 658, and distal tubes 662, respectively. The housing 656 is then formed by injection molding material around and between the inserts 666 and 668. A valve seal expander 670 may be provided to help keep the duck-bill valve within the introducer valve 654 open. Further, locking threads 672 are preferably provided to interface with the introducer valve housing 654.

FIGS. 35A–D show various configurations of the multi-lumen sheath 660. In FIG. 35A, a three-lumen solid configuration having a larger high-pressure lumen 674 is shown. FIG. 35B illustrates a four-lumen embodiment which has an outer sheath 680 so that fluid may be passed between the sheath and the exterior of the four tubes within. FIG. 35C is similar to the four-lumen sheath of FIG. 35B, but includes a single large lumen 682 and a plurality of smaller lumens 684. Finally, FIG. 35D illustrates an arrangement of lumens having a central high-volume high-pressure lumen 686, and a plurality of smaller lumens 688 attached around the circumference in an even array.

Figure 37:
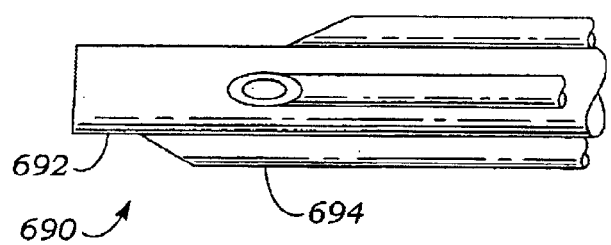
FIG. 37 is an elevational view of a further embodiment of a multi-lumen sheath for use in the device of FIG. 34.
Figure 38:
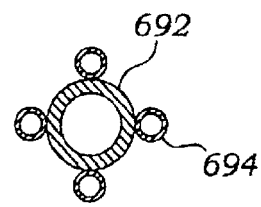
FIG. 38 is a sectional view of the multi-lumen sheath of FIG. 37.

FIGS. 37 and 38 illustrate a further embodiment of a multi-lumen sheath 690 having a central, high-pressure tube 692 and a plurality of outer or auxiliary tubes 694.

MLAD with Multiple Discrete Tubes

Figure 39:
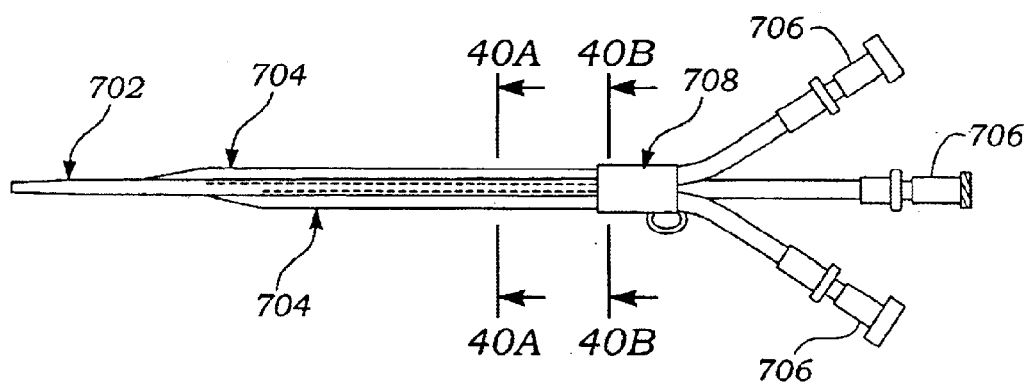
FIG. 39 is a plan view of a multiple lumen access device having a center tube and two side lumen tubes in accordance with the present invention.
Figure 40A:
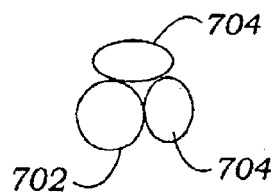
FIGS. 40A and 40B are sectional views of a sheath of the multiple lumen access device of FIG. 39 taken along lines 40A—40A and 40B—40B, respectively.
Figure 40B:
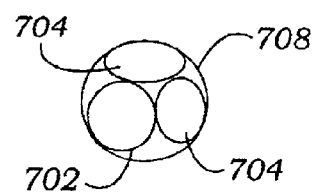

FIG. 39 illustrates a multi-lumen catheter device 700 having at least two discrete catheter tubes. In this embodiment, the multi-lumen catheter device 700 includes a main (or center) lumen tube 702 and two side lumen tubes 704. The lumen tubes 702 and 704 are configured in a side-by-side fashion, and proximal portions of the tubes 702, 704 are peeled apart to create sidearms. Hubs 706 may be attached to proximal ends of each lumen tube 702, 704 for fluid delivery or introduction of a medical device. Remote introducer valves may be connected to one or all the lumen tubes. Indeed, the device valves may be provided on any or all of the extension tubes for the various embodiments described herein and shown in any of the figures, including FIGS. 1, 6, 23A, 30. The catheter device 700 may further include a sleeve 708 at the region where the lumen tubes 702 and 704 branch outwardly. FIGS. 40A and 40B illustrate the different cross-sections of the device 700, the circular shape of the sleeve providing a smooth transition for sealing through a puncture wound into the skin. One of the advantages of this embodiment is that one or more of the lumen tubes 702 and 704 may be peeled off the multi-lumen catheter 700 if desired.

Figure 41:
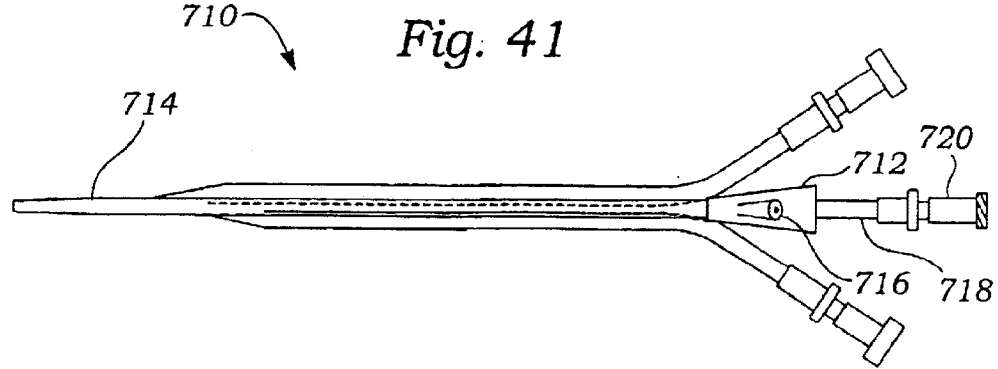
FIG. 41 is an alternative multiple lumen access device with discrete tubes as in FIG. 39 and having a junction housing.

FIG. 41 illustrates another alternative multi-lumen catheter device 710. This catheter device 710 is similar to the catheter device 700 illustrated in FIG. 39 and includes the additional feature of a junction housing 712 connected to a proximal end of a main lumen tube 714. The junction housing 712 receives a valve insert 716 and an extension tube 718 with a hub 720 connected to its proximal end. Again, the separate tubes can be peeled away to create various lumen devices.

Multiple Lumen Catheter through Introducer

FIGS. 42A and 42B illustrate a multi-function adapter 730 for connecting different components, for example, catheters and introducers, for use with the present invention. The multi-function adapter include a first unit and a second unit that are complementary and enable a quick-release connection of a multiple lumen device and an introducer. By way of example and not limitation, the multi-function adapter may include a female unit 730a and a male unit 730b. The male unit 730b includes at least one lug 732 extending radially outward, while the female unit 730a includes a slot (not illustrated) which accepts and interlocks with the lug. The slot may be a variety of configurations to securely interlock the male unit with the female unit, such as an L-shaped channel, a bayonet lock, an interference fit, etc. Other types of adapters known in the art such as luers may be utilized as long as components of the access device can be easily connected/disconnected.

In the embodiment of FIGS. 42A and 42B, the adapter 730 couples a multiple lumen catheter 734 with an introducer 735. The catheter 734 may be a CCO catheter or other multiple-lumen device, and includes a junction housing 736 between a distal multi-lumen sheath 738 and a plurality of proximal extension tubes 740. The introducer 735 includes a hub 742 with a side arm 744 for introducing or withdrawing fluids. The female unit 730a is adapted to fit over the sheath 738 by a press fit, adhesive, or any other means generally known in the art. Conversely, the male unit may be fixedly attached to the sheath 738 or distal end of the junction housing 736 instead of the female unit, if desired. The adapter 730 permits detachability of the multiple lumen catheter 734 from the introducer 735 and provides great flexibility in surgical or critical care situations.

FIGS. 43A and 43B illustrate a multiple-lumen access device 760 very similar to the device of FIGS. 42A and 42B but with the adapter formed as part of a multiple lumen catheter junction housing. The access device 760 includes an introducer 762 connected to a Central Venous Catheter (CVC) or other multiple lumen catheter 764 by a multi-function adapter 766a and 766b. The catheter 764 includes a multiple-lumen sheath 768 connected to a junction housing 770.

The access device 760 (and the device of FIG. 42) offers a significant advantage over current catheter designs in terms of cost saving and manner in which the access device 760 may be utilized. Currently, an introducer is inserted into a vein, and a surgical procedure is performed. After the surgical procedure, the introducer is usually removed and a new catheter is inserted in the vein through a second puncture and sutured onto the skin. The patient is then transported to a recovery room. By using the access device 760 of the present invention illustrated in FIG. 43, the procedure can be greatly simplified. The introducer 762 is first positioned in the vessel using traditional methods, such as the Seldinger technique. After the introducer 762 is used for sampling or infusing fluids, multiple lumen catheter 764 is inserted and utilized. The catheter 764 can then be detached from the introducer 762 and removed from the vessel while the introducer 762 is left in the vessel, and the introducer 762 now functions as a catheter. Thus, after the surgical procedure, the introducer 762 does not have to be removed from the vessel and a new catheter does not have to be inserted through a second puncture.

FIGS. 44A and 44B illustrate a multiple lumen access device 780 having an introducer 782 connected to a triple lumen junction housing 784 by a multi-function adapter 786a and 786b. Instead of the elongated sheath as in the previous two embodiments, the junction housing 784 includes a short hollow obturator 788 that serves to hold open a hemostasis valve in a hub 790 of the introducer 782. The three lumens within the junction housing 784 communicate with the lumen of the obturator 788 to deliver fluids to the introducer lumen.

Figure 45A:
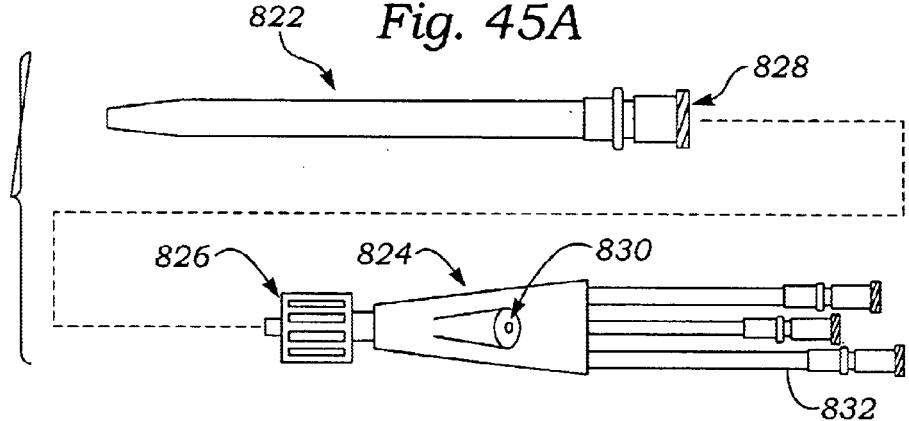
FIG. 45A is an exploded view of a multiple lumen access device having an introducer connected to triple lumen junction housing by a threaded adapter.
Figure 45B:
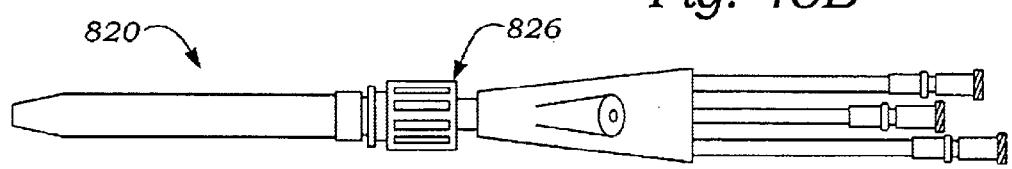
FIG. 45B is an assembled view of the multiple lumen access device of FIG. 45A.

FIGS. 45A and 45B illustrate an access device 820 having a single lumen introducer 822 connected to a multiple lumen junction housing 824 by a threaded female adapter 826 and male luer connection 828. A device valve 830 in the junction housing 824 permits insertion of various devices into a vessel via the introducer 822 at the same time that various fluids are infused through extension tubes 832.

Figure 46A:
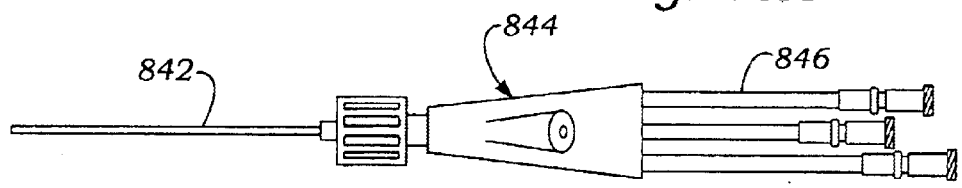
FIG. 46A is an exploded view of a multiple lumen access device having an introducer connected to triple lumen junction housing and elongated infusion tube by a threaded adapter.
Figure 46B:
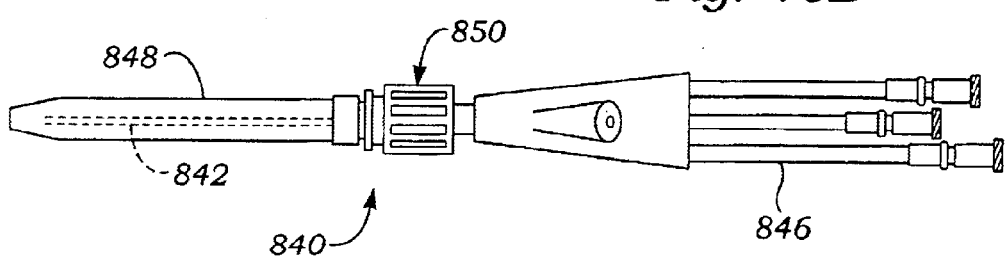
FIG. 46B is an assembled view of the multiple lumen access device of FIG. 46A.

FIGS. 46A and 46B illustrate an access device 840 similar to the access device 820 illustrated in FIG. 45 and includes the additional feature of a small diameter catheter tube 842 extending from a distal end of a junction housing 844. The catheter tube 842 functions as an infusion lumen for one of the extension tubes 846, while the space between the catheter tube 842 and a single lumen introducer 848 functions as a device lumen. Again, the junction housing 844 is attached to the introducer 848 with a threaded adapter 850.

Introducer within Introducer Combination

Figure 47A:
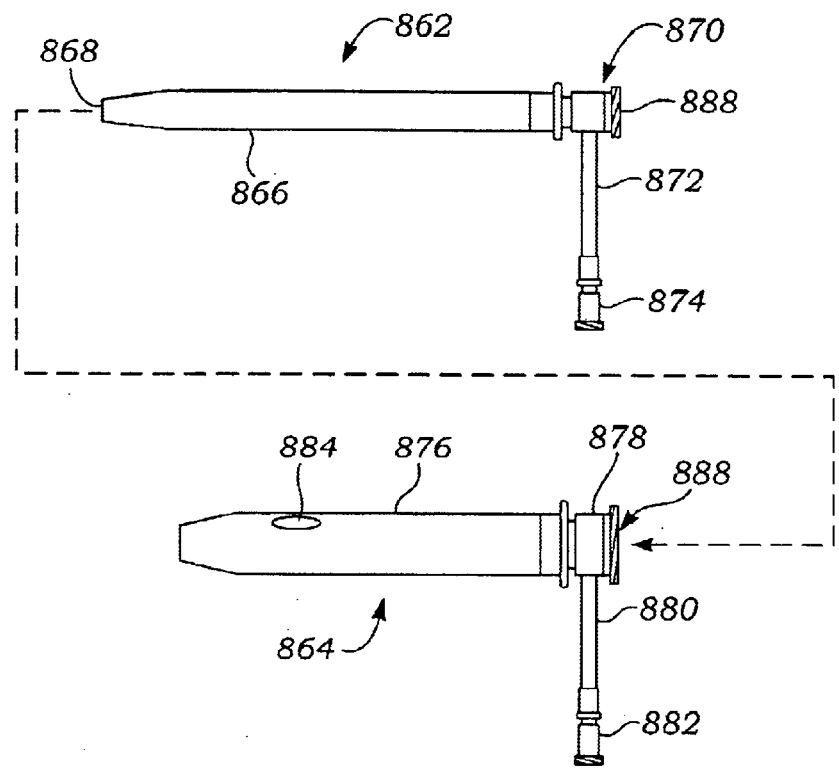
FIG. 47A is an exploded view of a multiple lumen access device having an introducer with infusion port telescopically fitting within a larger introducer.
Figure 47B:
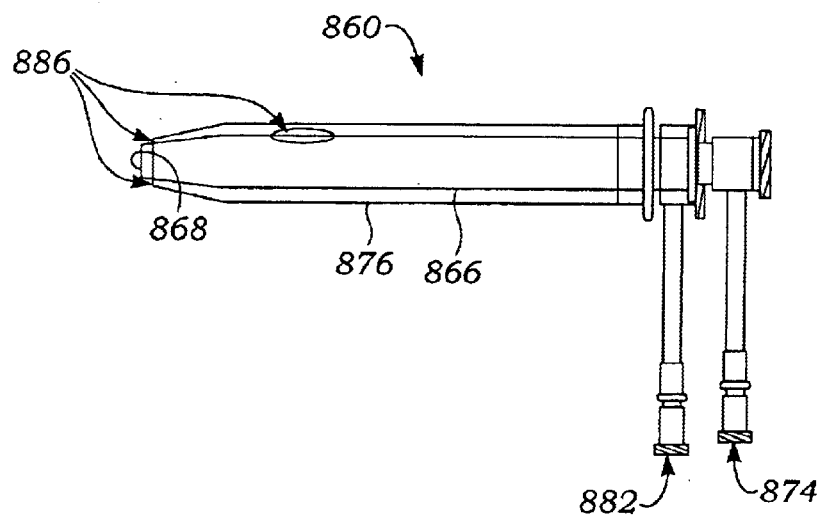
FIG. 47B is an assembled view of the multiple lumen access device of FIG. 47A.

A multiple lumen access to the body through a single patient entrance site may also be accomplished by using a plurality of elongated sheaths and implements, such as introducers, obturators or catheters, inserted coaxially within each other to form multiple independent lumens. FIGS. 47A and 47B, for example, illustrate a multi-lumen access device 860 comprising a first single-lumen introducer 862 telescopically received within a second single-lumen introducer 864. The first introducer 862 includes a single lumen sheath 866 having an opening 868 at its distal end and connected to an introducer valve housing 870 at its proximal end. Within the introducer valve housing, a duck-billed valve or other appropriate valves may be provided to seal the lumen from the exterior. The introducer valve housing 870 may include a side port extension tube 872 terminating in a hub 874 for attaching to infusion fluid sources. The second elongated implement, for example, an introducer 864 includes a single lumen sheath 876 connected to the distal end of an introducer valve housing 878. The introducer valve housing 878 also may include a side port extension tube 880 terminating in a hub 882 for attaching to infusion fluid sources, and the sheath 876 may include an opening 884 towards a distal end thereof to allow exit of fluid which has been introduced through the side port extension tube 880.

As shown in FIG. 47B, the sheath 866 of the first introducer 862 is sized to fit coaxially through the introducer valve 878 and lumen of the second introducer 864. The distal opening 868 of the first introducer sheath 866 may extend beyond the distal end of the second introducer sheath 876. In addition, at least one of the lumens formed by the placement of introducer 862 coaxially within the introducer 864 is capable of passing a supplemental catheter. By way of example and not limitation, one such catheter has an outside diameter sized about 4 French or more. In one exemplary application of FIG. 47B, fluid 1 (for example, medicine 1) may be introduced through the hub 882 and may exit the device through the opening 884 while fluid 2 (for example, medicine 2) may be introduced through the hub 874 and exit the device through the opening 868. Alternatively, the fit between the smaller sheath 866 and larger sheath 876 may be somewhat loose at the distal end so that fluid introduced through hub 882 may pass through an annular space formed therebetween, and through the opening 884, as indicated by the arrows 886. Both introducers 862 and 864 include male luer connectors 888 on their proximal ends for connecting to a variety of medical implements, including the threaded adapters for attaching multiple lumen catheters as previously described.

The access device 860 offers a significant advantage over known introducers by providing multiple lumen access with only a single patient entrance site. Currently, two introducers are usually inserted into the patient at two different sites if another independent lumen is required. The access device 860 of the present invention allows the flexibility to start a procedure with only one introducer 864, and if another independent lumen is required, an additional introducer 862 can be inserted into the introducer 864. It is noted that the access device is not limited to two introducers. For example, a combination of three or more introducers may be coaxially configured if additional independent lumens are required.

Also, as will be understood by those skilled in the art, at least one of the single lumen introducers that is coaxially inserted into another single lumen introducer may be made from a flexible deformable material. As a result, the wall forming the sheath of such insertable introducer will also form at least one of the multiple lumens and will be movable upon differential changes in pressure across the wall. This follows from the principles described earlier with respect to extruded multiple lumen sheaths, including the descriptions related to FIGS. 3A–B, 11A–C, 12 and 17. For instance, the larger introducer sheath 876 may be rigid, while the smaller introducer sheath 866 may be flexible or pliable. If a large amount of fluid is infused through larger introducer hub 882, the space around the smaller sheath 866 experiences an increase in pressure and the sheath may buckle inward to accommodate the larger flow. In one embodiment, a portion of the inside introducer may be rigid and some portion may be flexible, for example only the distal tip of the smaller introducer is rigid to permit insertion through the larger introducer.

MLADS Formed with Obturators within Introducers

Figure 48A:
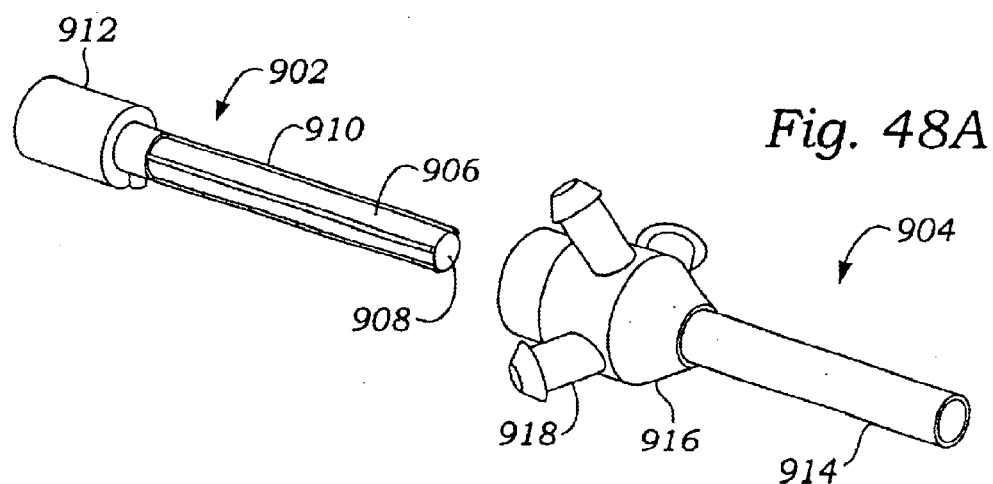
FIG. 48A is an exploded view of a multiple lumen access device with a multi-ribbed hollow obturator telescopically fitting within an introducer with infusion ports.
Figure 48B:
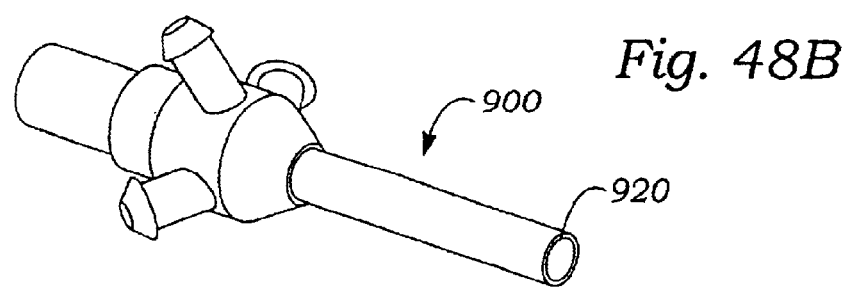
FIG. 48B is an assembled view of the multiple lumen access device of FIG. 48A.

Another alternative embodiment of the present invention forms multi-lumen access device by a combination of a single lumen catheter or introducer with a solid or hollow obturator. FIGS. 48A and 48B illustrate a multi-lumen access device 900 comprising an elongated implement, for example a multi-channel obturator 902, inserted into a single lumen sheath or catheter 904. The obturator 902 includes a sheath 906 having a device lumen 908 and, in one preferred embodiment, three evenly circumferentially arranged longitudinal ribs 910 extending radially from a proximal end to a distal end of the sheath 906. Any number of the radially extending ribs is within the scope of the present invention. Similarly, the ribs does not have to be arranged evenly circumferentially. A hemostasis valve 912 (within housing) is connected to the proximal end of the sheath 906. The catheter 904 includes a single lumen sheath 914 connected to a hemostasis valve 916 (within housing) with three access ports 918 for infusion of fluids.

When the obturator 902 is inserted into the catheter 904, as shown in FIG. 48B, the ribs 910 contact the inner wall of the catheter sheath 914 and form three (or any other desired number) auxiliary lumens 920. Each auxiliary lumen 920 communicates with the corresponding access port 918 of the catheter 904. To provide a liquid tight seal at the interface between the ribs 910 and inner wall of the catheter sheath 914, the obturator sheath 906 is made from a sufficiently rigid material and is sufficiently sized while the catheter sheath 914 is made from a sufficiently resilient material. Thus, the access device 900 has multiple independent fluid entries and multiple independent lumens. In addition, the obturator may be used as a fluid delivery lumen by having an obturator without a hemostasis valve. The multi-lumen access device 900 should have at least two auxiliary lumens 920, and preferably three, though other numbers of lumens are also within the scope of the present invention.

One of the advantages of the access device 900 over known introducer products is that it provides greater flexibility of use and eliminates the need for a central venous catheter (CVC). The prior art introducer is inserted into the patient; and if another independent lumen is required, a CVC is usually inserted into the patient. By using the access device 900, the catheter 904 is inserted into the patient and if another independent lumen is required as well as a device lumen, the obturator 902 may be inserted into the catheter 904 to achieve multi-lumen access with only one patient entrance site.

Figure 49:
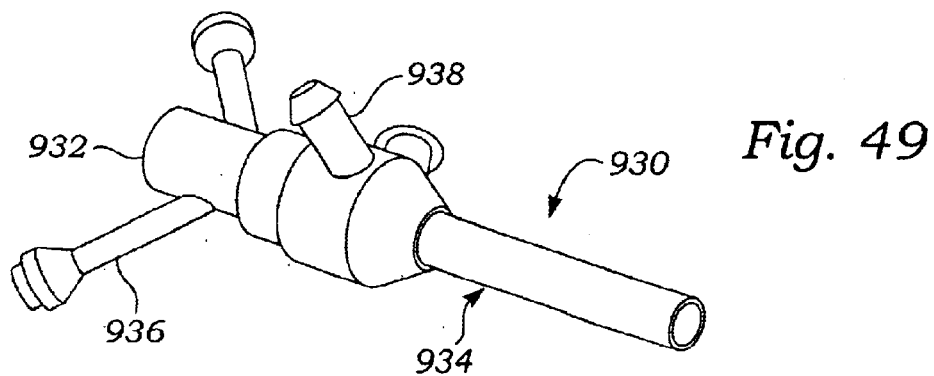
FIG. 49 is an assembled view of a multiple lumen access device similar to that shown in FIG. 48B with infusion ports formed on a hub of the multi-ribbed hollow obturator.

FIG. 49 illustrates another multi-lumen access device 930 which is similar to the access device 900 shown in FIGS. 48A and 48B with the exception that an obturator 932 has two access ports 936 for infusion of fluids, and a single lumen catheter 934 has only one access port 938. This arrangement allows all or some of the fluid to be introduced via the obturator 932 instead of the catheter 934. The remaining elements of the access device 930 are not discussed because they are essentially the same as the elements shown in FIGS. 48A and 48B.

A further alternative MLAD using a solid obturator or solid elongated implement is shown in FIGS. 50A and 50B. In this embodiment, a single lumen catheter or introducer 950 is converted to a multiple lumen access device 952 upon combination with an obturator 954. Obturator 954 comprises a proximal hub 956 and an elongated trefoil portion 958 that closely fits within a sheath 960 of the introducer 950. Three exemplary auxiliary lumens 962 are thus formed within the sheath 960. Three infusion ports 964 provide access to the lumens 962, and any one of them may be adapted to introduce a device through the introducer 950.

FIGS. 51–54 illustrate a still further MLAD embodiment formed using an obturator within an introducer. Specifically, a MLAD 970 is formed by the combination of a hollow obturator 972 with an introducer 974. The obturator includes a proximal hub 976 and a distal tube 978 having a plurality of outwardly directed ribs 980. A distal plug member 982 has a diameter the same as the rubs 980. The obturator 972 defines a hollow through bore extending through the proximal hub 976 and distal tube 978. The introducer 974 includes a proximal hub 986 and distal sheath 988, and also defines a hollow bore therethrough that transitions from a larger proximal diameter to a smaller distal diameter at a step 990. The sheath 988 has a tapered distal tip 992 and an outlet port 994 in one side. A fluid infusion port 996 is provided in the hub 986.

The distal tube 978 closely within the sheath 988, as seen in FIG. 52, until the plug member 982 abuts the internal step 990. The ribs 980 seal against the interior of the bore of the sheath 988 and thus three sealed fluid flow channels are formed between the obturator 972 and introducer 974. Either multiple outlet ports 994 may be provided, one for each channel, of the obturator may be rotated to place one of the three channels into communication with a single outlet port. Devices or other implements can be inserted through the bore 984 while fluid is infused through the channels. Another difference between this embodiment and those previously described is the provision of the tapered distal tip 992 on the introducer 974 that facilitates insertion over a dilator and into a vessel.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

What is claimed is:

1. A multiple lumen access system for use in providing an entry port into human body for selectively introducing medical devices therethrough and for providing auxiliary access into the body, the system including a multiple lumen access device comprising:

an outer tube which has a distal end for introduction into the body and a proximal end;

a device lumen defined within the outer tube, the device lumen having a distal end and a proximal end, wherein medical devices may be passed through the device lumen;

an auxiliary lumen defined within the outer tube and separately from the device lumen, the auxiliary lumen having a distal end and a proximal end;

a flexible wall located within the outer tube having a distal end and a proximal end and opposite sides, wherein one side of the wall partly defines the device lumen and the other side of the wall partly defines the auxiliary lumen, the wall being sufficiently flexible to be movable from a first position, where the device lumen at the particular location has a first cross-sectional area, to multiple flexed positions, where the device lumen at the particular location has corresponding multiple cross-sectional areas which are greater than or less than the first cross-sectional area of the device lumen; and a junction housing having a proximal end and a distal end to which the proximal end of the outer tube connects, the junction housing including a main channel in fluid communication with the device lumen and an auxiliary channel in fluid communication with auxiliary lumen, the main channel and auxiliary channel diverging from each other to be non-intersecting in the junction housing, wherein the outer tube is relatively stiff in relation to the flexible wall to facilitate introduction of the outer tube into a human body.

2. The multiple lumen access system of claim 1 further comprising a device lumen valve adjacent the proximal end of the device lumen to provide sealing of the device lumen when medical devices are both present and absent from the device lumen.

3. The multiple lumen access system of claim 1 further comprising a fluid reservoir connected to the proximal end of the auxiliary lumen.

4. The multiple lumen access system of claim 1 wherein the junction housing is made of a soft, flexible material.

5. The multiple lumen access system of claim 1 further comprising a device lumen valve to provide sealing of the device lumen when medical devices are both present and absent from the device lumen, wherein the device lumen valve is provided as part of the junction housing and is in fluid communication with the main channel.

6. The multiple lumen access system of claim 5 further including a device channel in the junction housing formed at an angle with the main channel and terminating at an internal end in fluid communication with the main channel, the device lumen valve being positioned at an external end of the device channel so that medical devices may be inserted therethrough and enter the main channel at an angle.

7. A multiple lumen access system of claim 6 wherein the main channel extends from the distal end of the junction housing and opens at the proximal end of the junction housing enabling introduction of fluids therethrough to the main channel.

8. A multiple lumen access system according to claim 5 wherein the device lumen valve is molded separately from the junction housing of a material more rigid than the junction housing and is assembled with the multiple lumen access device by insertion in a cavity formed in the junction housing.

9. A multiple lumen access system according to claim 8 further including a device channel in the junction housing formed at an angle with the main channel and terminating at an internal end in fluid communication with main channel, the device lumen valve being positioned in the cavity at an external end of the device channel so that medical devices may be inserted therethrough and enter the main channel at an angle.

10. A multiple lumen access system according to claim 9 wherein the main channel extends from the distal end of the junction housing and opens at the proximal end of the junction housing enabling introduction of fluids therethrough to the main channel.

11. A multiple lumen access system of claim 5, wherein the device lumen valve has a contact face with at least one groove, and further comprising;
  a contamination shield adapter having a contact face with at lease one lug such that the lug mates with groove when the adapter engages with the device lumen valve and provides a tactile feel to an operator when the adapter is properly engaged with the device lumen valve, the adapter being suitable for connecting a contamination shield to the device lumen valve.

12. A multiple lumen access system according to claim 1 wherein the main channel and auxiliary channel are oriented substantially coplanar so that the junction housing is substantially flat, and further including an extension tube extending from the proximal end of the junction housing and in fluid communication with main channel wherein a device lumen valve is connected to the extension tube to therefore be in fluid communication with the main channel.

13. A multiple lumen access system according to claim 12 further including a side port in the device lumen valve enabling infusion of fluids to the extension tube and main channel.

14. A multiple lumen access system according to claim 12 further including mating threaded connectors between the device lumen valve and the extension tube enabling easy removal of the device lumen valve.

15. A multiple lumen access system according to claim 12 further including a second extension tube extending from the proximal end of the junction housing and in fluid communication with the auxiliary channel, and an auxiliary lumen valve connected to the second extension tube to therefore be in fluid communication with auxiliary lumen.

16. A multiple lumen access system of claim 12 further comprising a luer connector on the device lumen valve and an infusion syringe having a mating luer connector.

17. A multiple lumen access system of claim 1 wherein two auxiliary lumens are located within the outer tube of the multiple lumen access device.

18. A multiple lumen access system of claim 17 wherein the two auxiliary lumens are of different sizes.

19. A multiple lumen access system of claim 17 wherein one of the two auxiliary lumens is located between the other auxiliary lumen and the device lumen.

20. A multiple lumen access system of claim 17 wherein the distal ends of the two auxiliary lumens are located at different locations between the proximal and distal ends of the outer tube.

21. A multiple lumen access system of claim 1 wherein the auxiliary lumen has a maximum cross-section formed when the flexible wall is flexed away from the auxiliary lumen as far as possible, and the multiple lumen access device further includes an outlet for the auxiliary lumen formed in the outer tube, the outlet having an area that is greater than or equal to the maximum auxiliary lumen cross-section.

22. A multiple lumen access system of claim 1 wherein there are two of the flexible walls that together form and inner tube within the outer tube.

23. A multiple lumen access system of claim 22 wherein the inner tube has a distal end and a proximal end and an exterior surface and an interior surface, wherein the interior surface defines the device lumen, and wherein there are two of the auxiliary lumens located between the exterior surface of the inner tube and an interior surface of the outer tube.

24. A multiple lumen access system of claim 23 wherein the inner tube is connected to the interior surface of the outer tube at two locations to delineate the two auxiliary lumens.

25. A multiple lumen access system of claim 1 wherein at least one spacer rib is located on an interior surface of the outer tube for maintaining a space between the outer tube and the flexible wall.

26. A multiple lumen access system of claim 1 wherein the outer tube is made from a different material than the flexible wall.

27. A multiple lumen access system of claim 1 further comprising a medical device located within the device lumen.

28. A multiple lumen access system of claim 1 wherein the flexible wall is constructed from a material and with a shape that moves from the relaxed position toward the flexed positions upon a pressure differential between the auxiliary lumen and the device lumen, the movement being toward the device lumen, and wherein a deplacement response curve of the flexible wall in non-linear such that the wall resists substantial movement from small pressure differentials.

29. A multiple lumen access system of claim 28 wherein the flexible wall has a variable thickness with areas of weakness in bending created at thinner portions so that when a device is present in the device lumen the wall contacts the device substantially along a one line of contact to facilitate sliding of the device within the device lumen.

30. A multiple lumen access system for use in providing an entry port into the human body for selectively introducing medical devices therethrough and for providing auxiliary access into the body, the system including a multiple lumen access device comprising:
  a sheath defining a device lumen and at least one auxiliary lumen, both having a distal end and a proximal end, wherein medical devices may be passed through the device lumen; and
  a proximal junction housing made of a flexible material softer than the material of the sheath having a proximal end and a distal end to which the proximal end of the sheath connects, the junction housing including a main channel in fluid communication with the device lumen and an auxiliary channel in fluid communication with the auxiliary lumen, the main channel and auxiliary channel diverging from each other to be non-intersecting in the junction housing, the junction housing further defining a cavity on the proximal end in fluid communication with the main channel.

31. A multiple lumen access system according to claim 30 further including a device lumen valve attached to the junction housing so as to be in fluid communication with the device lumen of the sheath.

32. A multiple lumen access system according to claim 31 wherein the device lumen valve is molded separately from the junction housing of a material more rigid than the junction housing and assembled with multiple lumen access device by insertion in the cavity formed in the junction housing.

33. A multiple lumen access system according to claim 31 further including a device channel in the junction housing formed at an angle with main channel and terminating at an internal end in fluid communication with the main channel, the cavity being located at an outermost end of the device channel, the device lumen valve being positioned in the cavity so that medical devices may be inserted therethrough and enter the main channel at an angle.

34. A multiple lumen access system according to claim 31 wherein the device lumen valve comprises a multi-component valve insert with a two-part rigid outer housing and at least one elastomeric inner valve member within the housing.

35. A multiple lumen access system according to claim 34 wherein the two-part rigid outer housing includes a portion forming an outermost opening and having internal threads for coupling with adapters for introducing medical devices.

36. A multiple lumen access system according to claim 34 including an elastomeric duckbill valve and an elastomeric wiper gasket within the housing.

37. A multiple lumen access system according to claim 30 further including a flexible wall located within the sheath and having a distal end and a proximal end and opposite sides, wherein one side of the wall partly defines the device lumen and the other side of the wall partly defines the auxiliary lumen, the wall being sufficiently flexible to be movable from a relaxed position, where the device lumen at at particular location along its length has a first cross-sectional area, to multiple flexed positions, where the device lumen at the particular location has a corresponding multiple cross-sectional areas which are greater than or less than the first cross-sectional area of the device lumen, and wherein at the particular location the sheath has a cross-sectional area that remains substantially unchanged and any of the cross-sectional areas of the device lumen does not exceed the cross-sectional area of the sheath.

38. A method for selectively introducing a medical devices into a human body through a single entry port and for providing simultaneous auxiliary fluid access into the body, comprising:

providing a multiple lumen access device comprising:
an elongated body which has a distal end for introduction into the body and a proximal end;
a device lumen through which medical devices may be passed defined within the elongated body, the device lumen having a distal end and a proximal end;
an auxiliary lumen defined within the elongated body and separately from the device lumen, the auxiliary lumen having a distal end and a proximal end; and
a flexible wall located within the elongated body having a distal end and a proximal end and opposite sides, wherein one side of the wall partly defines the device lumen and the other side of the wall partly defines the auxiliary lumen, the wall being sufficiently flexible to be movable from a first position, where the device lumen at the particular location has a first cross-sectional area, to multiple flexed positions, where the device lumen at the particular location has corresponding multiple cross-sectional areas which are greater than or less than the first cross-sectional area of the device lumen, wherein the elongated body is relatively stiff in relation to the flexible wall to facilitate introduction of the elongated body into a human body;

introducing the multiple lumen access device into the body with the distal ends of the device lumen and the auxiliary lumen being positioned within a vasculature of the human body;
flowing a medical solution through the auxiliary lumen into the vasculature in the absence of a device in the device lumen to move the flexible wall from the first position to one of the flexed positions;
inserting a medical device through the device lumen into the vasculature; and
flowing a medical solution through the auxiliary lumen into the vasculature with a device present in the device lumen.

39. The method of claim 38 further comprising the step of providing the multiple lumen access device with a fluid reservoir connected to the proximal end of the auxiliary lumen.

40. The method of claim 38 further comprising the step of providing the multiple lumen access device with a device lumen valve to provide sealing of the device lumen when medical devices are both present and absent from the device lumen.

41. The method of claim 40 further comprising the step of providing the multiple lumen access device with a junction housing having a proximal end and a distal end to which the proximal end of the elongated body connects, the junction housing including a main channel in fluid communication with the device lumen and an auxiliary channel in fluid communication with the auxiliary lumen, the main channel and auxiliary channel diverging from each other to be non-intersecting in the junction housing.

42. The method of claim 41 wherein the device lumen valve is provided as part of the junction housing and is in fluid communication with the main channel.

43. The method of claim 42 further comprising the step of providing the multiple lumen access device with a device channel in the junction housing formed at an angle with main channel and terminating at an internal end in fluid communication with the main channel, the device lumen valve being positioned at an external end of the device channel so that medical devices may be inserted therethrough and enter the main channel at an angle.

44. The method of claim 43 wherein the main channel extends from the distal end of the junction housing and opens at the proximal end of the junction housing enabling introduction of fluids therethrough to the main channel.

45. The method of claim 42 wherein the device lumen valve is molded separately from the junction housing of a material more rigid than the junction housing and is assembled with the multiple lumen access device by insertion in a cavity formed in the junction housing.

46. The method of claim 42 further comprising the step of providing the multiple lumen access device with a device channel in the junction housing formed at an angle with the main channel and terminating at an internal end in fluid communication with the main channel, the device lumen valve being positioned in the cavity at an external end of the device channel so that medical devices may be inserted therethrough and enter the main channel at an angle.

47. The method of claim 46 wherein the main channel extends from the distal end of the junction housing and opens at the proximal end of the junction housing enabling introduction of fluids therethrough to the main channel.

48. The method of claim 41 wherein the main channel and auxiliary channel are oriented substantially coplanar so that the junction housing is substantially flat, and further including and extension tube extending from the proximal end of the junction housing and in fluid communication with the main channel wherein the device lumen valve is connected to the extension tube to therefore be in fluid communication with the main channel.

49. The method of claim 48 further comprising the step of providing the multiple lumen access device with a side port in the device lumen valve enabling infusion of fluids to the extension tube and main channel.

50. The method of claim 48 further comprising the step of providing the multiple lumen access device with mating threaded connectors between the device lumen valve and the extension tube enabling easy removal of the device lumen valve.

51. The method of claim 50 further comprising the step of providing the multiple lumen access device with a luer connector on the device lumen valve and an infusion syringe having a mating luer connector.

52. The method of claim 38 wherein two auxiliary lumens are located within the elongated body of the multiple lumen access device.

53. The method of claim 52 wherein the distal ends of the two auxiliary lumens are located at different locations between the proximal and distal end of the elongated body.

54. The method of claim 38 wherein the multiple lumen access device comprises an inner tube formed by two of the flexible walls located within the elongated body, the inner tube having a distal end and a proximal end, and the inner tube having and exterior surface and an interior surface wherein the interior surface defines the device lumen, and two auxiliary lumen located between the exterior surface of the inner tube and an interior surface of the elongated body.

55. The method of claim 54 wherein the inner tube is connected to the interior surface of the elongated body at two locations to delineate the two auxiliary lumens.

56. The method of claim 38 further wherein the elongated body is made from a different material than the flexible wall.

57. The method of claim 38 further comprising the steps of:

provising a device lumen valve adjacent the proximal end of the device lumen to provide sealing of the device lumen when medical devices are both present and absent from the device lumen, the device lumen valve having a contact face with at least on groove;

providing an adapter having a contact face with at least one lug such that the lug mates with the groove when the adapter engages with the device lumen valve and provides a tactile feel to an operator when the adapter is properly engaged with the device lumen valve; and connecting a contamination shield to the adapter.

* * * * *

UNITED STATES PATENT AND TRADEMARK OFFICE
CERTIFICATE OF CORRECTION

PATENT NO.    : 6,827,710 B1
DATED         : December 7, 2004
INVENTOR(S)   : Charles R. Mooney et al.

It is certified that error appears in the above-identified patent and that said Letters Patent is hereby corrected as shown below:

Column 12,
Line 20, after "may be," delete "infused removed" and insert -- infused/removed. --.

Column 14,
Line 54, after "formed," insert -- by. --.

Column 15,
Line 10, delete "MLADJ" and insert -- MLAD. --.

Column 16,
Line 33, after "Conversely, the" delete "fame" and insert -- frame. --.

Column 26,
Line 3, after "port into," insert -- the. --.
Line 31, after "communication with," insert -- the. --.

Column 27,
Line 22, before "one lug," delete "lease" and insert -- least. --.

Column 28,
Line 7, after "together form," delete "and" and insert -- an. --.
Line 33, after "and wherein a," delete "deplacement" and insert -- displacement. --.
Line 34, after "flexible wall," delete "in" and insert -- is. --.

Column 30,
Line 67, before "extension," delete "and" and insert -- an. --.

UNITED STATES PATENT AND TRADEMARK OFFICE
CERTIFICATE OF CORRECTION

PATENT NO. : 6,827,710 B1
DATED : December 7, 2004
INVENTOR(S) : Charles R. Mooney et al.

It is certified that error appears in the above-identified patent and that said Letters Patent is hereby corrected as shown below:

Column 32,
Line 2, before "exterior," delete "and" and insert -- an. --.

Signed and Sealed this

First Day of November, 2005

JON W. DUDAS
*Director of the United States Patent and Trademark Office*